United States Patent [19]

Scarborough et al.

[11] Patent Number: 5,344,783
[45] Date of Patent: Sep. 6, 1994

[54] PLATELET AGGREGATION INHIBITORS

[75] Inventors: Robert M. Scarborough, Hayward; Israel F. Charo, Lafayette, both of Calif.

[73] Assignee: COR Therapeutics, Inc., South San Francisco, Calif.

[21] Appl. No.: 91,392

[22] Filed: Jul. 12, 1993

Related U.S. Application Data

[63] Continuation of Ser. No. 685,997, Apr. 12, 1991, abandoned, which is a continuation of Ser. No. 367,509, Jun. 16, 1989, abandoned.

[51] Int. Cl.$^5$ .......................................... G01N 33/566
[52] U.S. Cl. .................................. 436/501; 436/503; 436/504; 436/69; 435/7.1; 435/7.8; 435/7.93; 435/13
[58] Field of Search ................. 436/501, 503, 504, 69; 435/7.1, 7.8, 7.93, 13

[56] References Cited

FOREIGN PATENT DOCUMENTS 0319506  6/1989  European Pat. Off. .
0341915  11/1989  European Pat. Off. .
9807609  8/1989  PCT Int'l Appl. .

OTHER PUBLICATIONS

Nachman et al (1982) *J. Clin. Invest* 69, 263–269.
Bennett et al (1983) *Proc. Natl. Acad. Sci.* 80, 2417–2421.
Phillips et al. (1988) *Blood* 71, 831–843.
Samanen et al., *J. Cell. Biol.* (1990) Supplement 14A-:A229.
Dennis et al., *Proc. Natl. Acad. Sci.* (1989) 87:2471–2475.
Shebuski et al., *J. Biol. Chem.* (1989) 264(36):21550–21556.
Ali et al., *Peptides: Chemistry, Structure and Biology* (Proceedings of the 11th American Peptide Symposium), Marshall, G. R. and River, J. E. editors, EX-COM, Leiden (1990).

*Primary Examiner*—Keith Baker
*Attorney, Agent, or Firm*—Cooley Godward Castro Huddleson & Tatum

[57] ABSTRACT

An assay for screening snake venom for the presence or absence of platelet aggregation inhibitors (PAIs) based on specific receptor binding is described. Using this assay, the identification and characterization of the PAI in a wide range of snake venom samples were accomplished. The purified PAI from several of these active snake venoms is described. In addition, PAIs lacking the Arg-Gly-Asp adhesion sequence but containing Lys-Gly-Asp are prepared and shown to specifically inhibit the binding of fibrinogen or von Willebrand Factor to GP IIb–IIIa.

3 Claims, 20 Drawing Sheets

EAGEECDCGSPENPCCDAATCKLRPGAQCADGLCCDQCRFMKKGTVCRVAKGDWNDDTCTGQSADCPRNGLYG PE-SB
*Sistrurus m. barboun PAI*

EAGEECDCGSPENPCCDA...

DAATCKLRPGAQCA... Asp-N-1

DQCRFMKKGTVCRVAKG -2

DCPRNGLYG -3

GDWNDDTCTGQSADCPRNGLYG Lys-C-1

LRPGAQCADGLCCDQCRFMK -2

```
                   10         20         30         40         50         60         70
                   :          :          :          :          :          :          :
Barbourin    EAGEECDCGSPENPCCDAATCKLRPGAQCADGLCCDQCRFMKKGTVCRVAKGDWNDDTCTGQSADCPRNGLYG
Trigramin        D          A           I              GE          S IEE    I R  DL Y N R  G  PFH--
Elegantin                   A                                        K R I  R R  NP   R           -
Albolabrin       D          A           I              GE          S        I RR DL Y N I  G  P HA
Flavoviridin --             S                                              XX R I  I R  FP  R  L NG  XNDL-
Echistatin   ----------------E ES P RN K L E  I KR R  DM  Y N KTC  PHKGPAT
```

PLATELET AGGREGATION INHIBITORS

CROSS REFERENCE TO RELATED APPLICATIONS

This application is a continuation of U.S. application Ser. No. 07/685,997, filed Apr. 12, 1991, now abandoned, which is a continuation of U.S. application Ser. No. 07/367,509 filed Jun. 16, 1989, now abandoned.

TECHNICAL FIELD

This invention relates to a group of polypeptides isolated and purified from various snake venoms which are useful as therapeutic agents for the treatment of and prevention of platelet-associated ischemic disorders. More specifically, the invention concerns peptides which block specific receptors for adhesive proteins involved in platelet adherence and aggregation. Furthermore, this invention describes methods for detecting, and purifying said polypeptides to substantial homogeneity from snake venoms, as well as processes for preparing the polypeptides both synthetically and through the use of recombinant DNA methods.

BACKGROUND ART

Heart disease is the primary cause of death in most western societies. The most prevalent heart disease states are related to platelet-dependent ischemic syndromes, including, but not limited to atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation either on vessel walls or within the lumen by blood-borne mediators.

Circulating platelets have been shown to play a central role in the response to a variety of blood vessel injuries, such as narrowing of the lumen, plaque formation, and the presence of foreign bodies (e.g., catheters) and the like. The response of platelets to these injuries is a sequence of events including platelet adherence, platelet aggregation, formation of microthrombi, and release of platelet granular components, including potent cellular mitogenic factors. There is a variety of pathologies that can occur from this sequence of events, including a variety of atherosclerotic and thrombotic phenomena.

Integral to platelet function is the platelet membrane glycoprotein (GP) IIb–IIIa complex which constitutes the fibrinogen (Fg), von Willebrand Factor (vWF), and fibronectin (Fn) receptor on activated platelets (see Phillips et al., Blood (1988) 71:831–843). Platelet GP IIb–IIIa is now known to be a member of a superfamily of structurally and functionally related adhesive protein receptors known collectively as the "integrins". Many stimuli have been identified which are thought to activate the GP IIb–IIIa receptor on the platelet surface and thus lead to the aggregation of platelets in vivo, and ultimately to the formation of thrombi. These stimuli include ADP, epinephrine, thrombin, collagen and thromboxane $A_2$. The activated GP IIb–IIIa complex on stimulated platelets binds the adhesive proteins Fg, Fn and vWF; however, it is the binding of fibrinogen that is believed to be principally responsible for platelet aggregation and thrombus formation in vivo. Therefore, substances which specifically inhibit the binding of fibrinogen to GP IIb–IIIa inhibit platelet aggregation and could be candidates for inhibiting thrombus formation in vivo.

Short peptides derived from the sequences of Fg, Fn and vWF have been disclosed which block the binding of these adhesive proteins to activated platelets and inhibit platelet aggregation (see Hawiger et al., U.S. Pat. Nos. 4,661,471; and Rouslahti et al., U.S. Pat. No. 4,614,517). One of these peptides is the sequence RGD, and the tetrapeptide sequence RGDS has been used specifically. The amino acid sequence RGDX is found in a variety of adhesive proteins and has been demonstrated to play an important role in the interaction with adhesive protein receptors. See, e.g., Pierschbacher et al., J Biol Chem (1987) 262:17294–17298; Ruggeri et al., Proc Natl Acad Sci (USA) (1986) 83:5708–5712; and Ruoslahti et al., Cell (1986) 44:517–518. A separate class of inhibitory peptides utilizes peptide sequences modeled on the carboxyl terminal sequence derived from the gamma chain of fibrinogen, the dodecapeptide HHLGGAQKAGDV (Kloczewiak et al., Biochemistry (1989) 28:2915–2919; Timmons et al., Ibid., 2919–2923). However, the usefulness of the RGD and dodecapeptide-based small peptides is limited because they either have a low affinity of interaction with platelet receptors ($IC_{50}=10-100$ uM) or interact with other adhesive protein receptors.

Recently, several groups have isolated and characterized low molecular weight polypeptide factors from snake venoms which have extremely high affinity for the GP IIb–IIIa complex on stimulated platelets. Huang, T.F., et al., J Biol Chem (1987) 262:16157–16163; Huang, T.F., et al., Biochemistry (1989) 28:661–666 report the fibrinogen and/or von Willebrand Factor platelet binding inhibition properties and primary structure of trigramin, a 72 amino acid peptide containing RGD and 6 disulfide bridges isolated from Trimeresurus gramineus. Gan, Z.-R., et al., J Biol Chem (1988) 263:19827–19832, report the properties and structure of echistatin, a 49 amino acid peptide also containing RGD and 4 putative disulfide bridges which is isolated from Echis carinatus. Williams, J. A., et al., FASEB Journal (1989) 3:A310, Abstr. No. 487m, report the related peptides elegantin, albolabrin, and flavoviridin. All factors thus far purified from snake venom which inhibit the binding of adhesive proteins to integrin receptors contain the RGD sequence.

Although these reported snake venom factors are potent platelet aggregation inhibitors in vitro, these peptides also bind with high affinity to other members of the adhesive protein receptors such as the vitronectin and fibronectin receptors (Knudsen, K. A., et al., (1988) Exp Cell Res 179:42–49). This lack of specificity of snake venom factors thus far identified for GP IIb–IIIa is an undesirable feature of their therapeutic use as inhibitors of thrombus formation.

Another approach for the generation of thrombus inhibitors has been the development of murine anti-GP IIb–IIIa receptor monoclonal antibodies which block the binding of the adhesive proteins to stimulated platelets. Use of these monoclonal antibodies to prevent coronary artery reocclusion after reperfusion with tissue plasminogen activator in dogs has been reported (Yasuda, T., et al., J Clin Invest (1988) 81:1284–1291).

Clearly, additional therapeutic treatment regimens are needed for preventing or at least mitigating undesirable thrombus formation. In particular, therapeutic agents capable of blocking or inhibiting thrombus formation at specific locations would provide major therapeutic benefits. Ideally, these agents will be potent, specific and nonimmunogenic to most patients; they should be easy to administer, stable and economical to produce. Further, these agents should act transiently and be capable of functioning at the earliest stages of thrombus formation, without interfering with long-term hemostasis. The present invention fills these and other related needs.

DISCLOSURE OF THE INVENTION

The invention provides a simple screening procedure to assess the ability of low molecular weight (<10kd) factors in snake venom or other biological sources to inhibit, specifically, thrombus formation mediated by platelet aggregation. This procedure takes advantage of the understanding that platelet aggregation is primarily effected through binding of fibrinogen to the receptor glycoprotein GP IIb-IIIa at the surface of platelets when the platelets are treated with appropriate stimuli, such as ADP. By using these criteria, i.e., inhibition of binding of fibrinogen to isolated receptor and analogous criteria related to inhibition of binding of fibronectin (Fn) to fibronectin receptor (Fn/FnR binding) and vitronectin to vitronectin receptor (Vn/VnR binding), as well as the binding of other factors, such as Fn and vWF to the GP IIb-IIIa receptor, a specificity profile for the platelet aggregation inhibitor (PAI) can be rapidly and conveniently obtained. This approach has been used to screen and characterize an extensive panel of snake venoms for the presence or absence of PAI, as well as to characterize the specificity of PAI from some members of the panel.

Accordingly, in one aspect, the invention is directed to a rapid screening method for the presence or absence of PAI in a biological fluid, which method comprises contacting the fluid with isolated GP IIb-IIIa receptor in a test reaction in the presence of fibrinogen and comparing the amount of fibrinogen bound to GP IIb-IIIa in the test reaction with the amount of fibrinogen bound to GP IIb-IIIa receptor in a control reaction. The method may further include test and control reactions which involve contacting Fn with Fn receptor, Vn with Vn receptor, Fn with GP IIb-IIIa, or vWF with GP IIb-IIIa in the presence and absence of the biological fluid to characterize the specificity of the PAI.

In another aspect, the invention is directed to novel PAI in isolated form which is identified in, and can be isolated from, active snake venom according to the methods of the invention. In particular, the invention relates to PAI, in isolated form, which can be isolated from *Eristicophis macmahonii; Agkistrodon rhodostoma, A. halys blomhoffi, A. hypnale, A. acutus, A. piscivorous leucostma, A. piscivorus conanti; Bothrops asper; Bothrops cotiara, B. jararaca, B. jararacussu, B. lansbergi, B. medusa, B. nasuta, B. neuwiedi, B. pradoi, B. schlegli; Crotalus atrox, C. basilicus, C. cerastes cerastes, C. durissus durissus, C. durissus totanatacus, C. horridus horridus, C. molossus molossus, C. ruber ruber, C. viridis cereberus, Crotalus v. helleri, Crotalus v. lutosus, Crotalus v. oreganus, Crotalus v. viridis; Lachesis mutas; Sistrurus catenatus tergeminus,* and *Sistrurus milarus barbouri.*

In a preferred aspect, the invention relates to PAI in isolated form which can be prepared from active snake venom identified by the method of the invention to specifically inhibit the binding fibrinogen (Fg) and/or von Willebrand Factor (vWF) to GP IIb-IIIa.

In still another preferred aspect, the invention relates to PAI in isolated form wherein the sequence responsible for binding to the adhesive protein receptor has the sequence KGD.

In other aspects, the invention is directed to recombinant materials and methods useful to produce the PAI of the invention.

In other aspects, the invention is directed to pharmaceutical compositions useful in inhibiting thrombus formation in an animal subject which contain an effective amount of the isolated PAI of the invention, and to methods to inhibit platelet aggregation and thrombus formation using these compositions.

BRIEF DESCRIPTION OF THE DRAWINGS

FIG. 11 shows the amino acid sequence of the PAI isolated in FIG. 9.

FIG. 12 shows a comparison of the amino acid sequence of *Sistrurus m. barbouri* PAI with other snake venom PAI.

FIG. 19A shows the effect of *Sistrurus m. barbouri* PAI barbourin. FIG. 19B shows the effect of *Eristicophus macmahoni* PAI eristicophin. FIG. 19C shows the effect of *Echis carnitus* PAI echistatin.

DETAILED DESCRIPTION OF THE INVENTION

Figure 1:
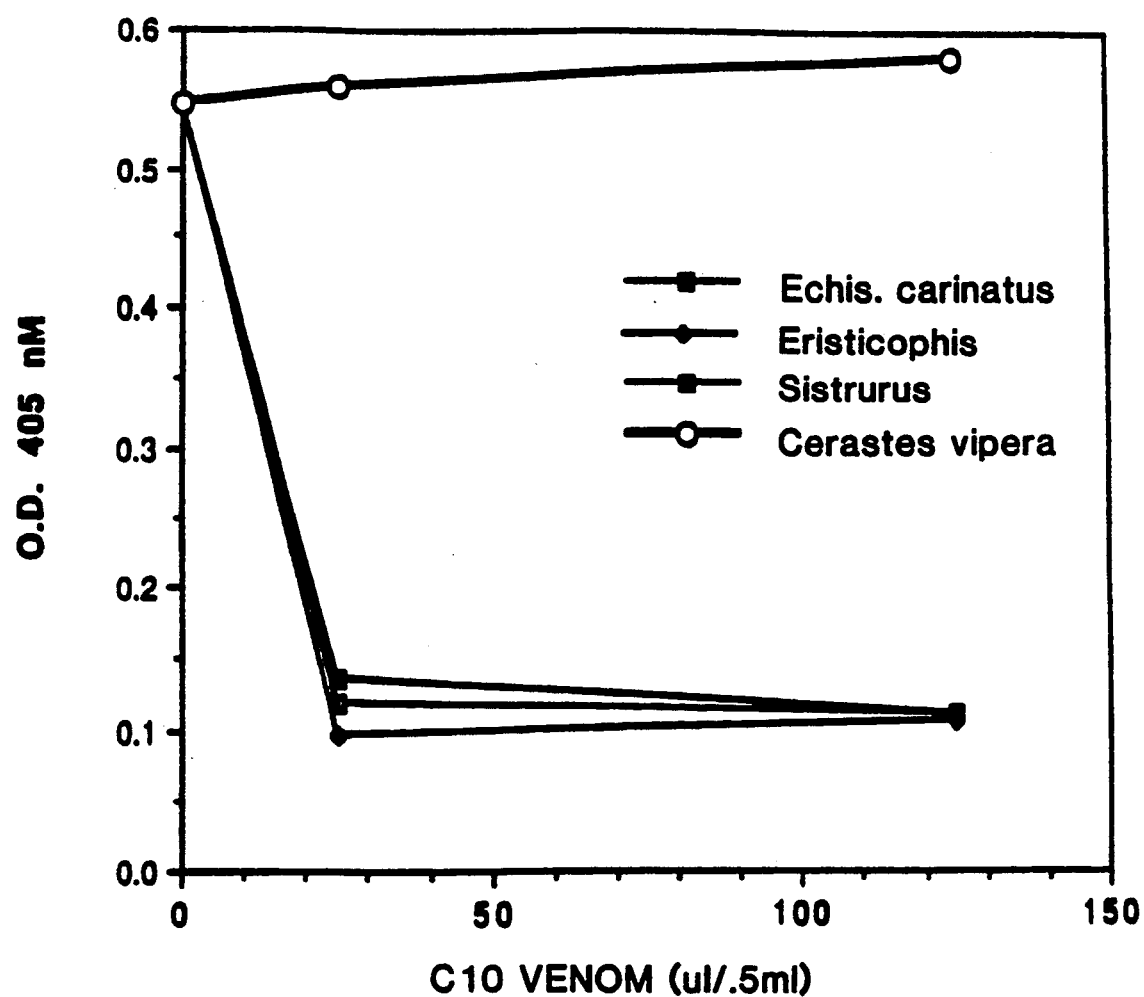
FIG. 1 shows inhibition of the binding of fibrinogen to GP IIb-IIIa by partially purified snake venoms.

The platelet aggregation inhibitors (PAI) of the invention are low molecular weight peptides which can be prepared in isolated form as described below, from snake venom which has been identified as "active", i.e., has been found to contain PAI using the method of the invention. By PAI is meant a factor which is capable of preventing the aggregation of stimulated platelets in standard assays, for example those described by Gan, Z. R., et al., and Huang, T.F., et al., (supra). In these assays, washed platelets are combined with fibrinogen, $Ca^{+2}$ and the material to be tested. The platelets are stimulated with ADP (or other known stimulators or combinations thereof) and aggregation (or lack thereof) is observed using, for example, a commercially available aggregometer.

Some of the PAI of the invention are identified as specific for the inhibition of binding of fibrinogen and/or vWF to GP IIb–IIIa. It is understood that specificity is a matter of degree; therefore, PAI "specific for inhibition of Fg or vWF binding to GP IIb–IIIa binding" inhibits this binding greatly more than it inhibits the binding of Fn to FnR, Vn to VnR, Fn to GP IIb–IIIa. By "greatly more" is meant that either the % inhibition is at least twofold greater or that the concentration of PAI that causes 50% inhibition is at least twofold less for Fg or vWF/GP IIb–IIIa binding inhibition than for alternate ligand/receptor binding.

The invention method permits ready identification and characterization of PAI in snake venom. Upon such identification, and, optionally and optimally, characterization, the PAI can be prepared in isolated form using a variety of standard techniques illustrated herein and disclosed in the art. For example, a combination of separation based on molecular weight (typically recovery of substances of <10 kd), ion exchange chromatography, and reverse phase HPLC can be used. Other techniques can also be employed, but a workable procedure applicable to PAI from any active snake venom is as follows:

About 10–1000 mg venom are dissolved in dilute acetic acid and applied to a sizing column, such as Sephadex G-50, and eluted in the same solvent. Fractions are assayed for activity using the Fg/GP IIb–IIIa binding assay of the invention or a standard platelet aggregation assay (PAA). Alternatively, the <10 kd fraction of the fraction of the venom can be uncovered using ultrafiltration.

The low MW fractions are then loaded onto a preparative C-18 HPLC column, such as a C-18 Delta Pak reverse phase HPLC column, available from Waters, preequilibrated in 0.1% trifluoroacetic acid (TFA)/8% acetonitrile. The adsorbed PAI is then eluted using a gradient of 8%–60% acetonitrile in 0.1% TFA. The slope of the gradient and flow rate are optimized using routine procedures. Active fractions are determined by PAA as described above or by the invention receptor binding method. The active fractions are then pooled, concentrated, and tested for homogeneity using analytical HPLC or SDS-PAGE. Further reverse-phase HPLC gradient purification is applied until the recovered PAI is homogenous.

The PAIs of the invention, obtainable by the foregoing or other purification methods include that from venoms selected from the group consisting of *Eristicophis macmahonii; Agkistrodon rhodostoma, A. halys blomhoffi, A. hypnale, A. acutus; Bothrops asper, Bothrops cotiara, B. jararaca, B. jararacussu, B. lansbergi, B. medusa, B. nasuta, B. neuwiedi, B. pradoi, B. schlegli; A. piscivorous leucostoma, A. piscivorus conanti; Crotalus atrox, C. basilicus, C. cerastes cerastes, C. durissus durissus, C. durissus totanatacus, C. horridus horridus, C. molossus molossus, C. ruber ruber, C. viridis cereberus, Crotalus v. helleri, Crotalus v. lutosus, Crotalus v. oreganus, Crotalus v. viridis; Lachesis mutas; Sistrurus catenatus tergeminus*, and *Sistrurus milarus barbouri*.

Particularly preferred are PAI isolated from *S. catenatus tergeminus, S. m. barbouri, Eristicophis macmahonii, Crotalus viridis viridis*, and *Lachesis mutas*. Particularly preferred are PAI specific for inhibiting Fg or vWF/GP IIb–IIIa binding, e.g., *S. m. barbouri*.

The purified PAI of the invention can be sequenced using standard procedures, thus permitting synthesis using standard solid phase techniques (in particular for shorter forms of the PAI) or recombinant production. For example, an Applied Biosystems Sequenator can be used following pyridylethylation as described by Huang et al., *J Biol Chem* (1987) 262:16157 ∝ 16163 and desalting on a C-18 Delta Pak column using 0.1% TFA and acetonitrile.

The DNA encoding the sequenced PAI is preferably prepared using commercially available nucleic acid synthesis. Methods to construct expression systems for production of PAI in recombinant hosts are generally known in the art.

Expression can be effected in either procaryotic or eucaryotic hosts. Procaryotes most frequently are represented by various strains of *E. coli*. However, other microbial strains may also be used, such as bacilli, for example *Bacillus subtilis*, various species of *Pseudomonas*, or other bacterial strains. In such procaryotic systems, plasmid vectors which contain replication sites and control sequences derived from a species compatible with the host are used. For example, a workhorse vector for *E. coli* is pBR322 and its derivatives. Commonly used procaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived $P_L$ promoter and N-gene ribosome binding site. However, any available promoter system compatible with procaryotes can be used.

Expression systems useful in eucaryotic hosts comprise promoters derived from appropriate eucaryotic genes. A class of promoters useful in yeast, for example, includes promoters for synthesis of glycolytic enzymes, e.g., those for 3-phosphoglycerate kinase. Other yeast promoters include those from the enolase gene or the Leu2 gene obtained from YEp13.

Suitable mammalian promoters include the early and late promoters from SV40 or other viral promoters such as those derived from polyoma, adenovirus II, bovine papilloma virus or arian sarcoma viruses. Suitable vital and mammalian enhancers are cited above. In the event plant cells are used as an expression system, the nopaline synthesis promoter, for example, is appropriate.

The expression systems are constructed using well-known restriction and ligation techniques and transformed into appropriate hosts.

Transformation is done using standard techniques appropriate to such cells. The cells containing the expression systems are cultured under conditions appropriate for production of the PAI, and the PAI is then recovered and purified.

The PAI of *Sistrurus m. barbouri* has been purified to homogeneity and sequenced. We have termed this peptide "barbourin". The complete amino acid sequence for this peptide is shown in FIG. 11. Unlike the adhesive proteins for GP IIb–IIIa so far identified and the peptides from snake venoms that block GP IIb–IIIa function, barbourin does not contain the standard Arg-Gly-Asp sequence of the adhesive proteins known in the art. The apparent binding sequence in barbourin is Lys-Gly-Asp(Trp). The presence of the KGD sequence in the apparent binding region of this peptide is especially surprising in view of the observation that replacement of Lys for Arg in small synthetic peptides based on the RDGX sequence greatly decreases the ability of these peptides to bind to integrin receptors (Pierschbacher et al., *Proc Natl Acad Sci* (USA) (1984) 81:5985–5988; Williams et al., *Thromb Res* (1987) 46:457–471). It is possible, although not established, that this substitution may in part be responsible for the specificity of the barbourin peptide to inhibit Fg and vWF binding to GP IIb–IIIa, versus vitronectin binding to the vitronectin receptor.

The availability of the purified PAI of the invention also permits the production of antibodies specifically immunoreactive with these forms of the active peptide.

The compositions containing purified PAI isolated from snake venom or otherwise synthesized can be used to stimulate the production of antibodies which immunoreact with the PAI peptide. Standard immunization protocols involving administering PAI to various mammals, such as rabbits, rats, mice, and sheep, result in antisera which are immunoreactive with the purified peptide. PAI may be advantageously conjugated to a suitable antigenically neutral carrier, such as an appropriate serum albumin or keyhole limpet hemocyanin, in order to enhance immunogenicity. Furthermore, the antibody-secreting cells of the immunized mammal can be immortalized to generate monoclonal antibody panels which can then be screened for reactivity with PAI.

The resulting polyclonal or monoclonal antibody preparations are useful in assays for levels of the corresponding PAI in biological samples using standard immunoassay procedures.

The Assay

The identification of snake venom starting material which contains active PAI, and which PAI has known specificity, is made possible by the assay of the invention. The assay rests on the observation that compounds which block the binding of fibrinogen to the GP IIb–IIIa complex in vitro also are capable of inhibiting thrombin or ADP-induced aggregation of human platelets and the formation of platelet-thrombi in vivo. This observation provides the basis for obtaining potent PAI by evaluating the ability of test materials to disrupt fibrinogen-GP IIb–IIIa interactions.

In the assay, GP IIb–IIIa, prepared in purified form, for example as described by Fitzgerald, L. A., et al., *Anal Biochem* (1985) 151:169–177, incorporated herein by reference, is coated onto a solid support such as beads, test tubes, or microtiter plates. The coated support is then contacted with fibrinogen and with the test material and incubated for a sufficient time to permit fibrinogen to bind to the receptor. The fibrinogen is typically provided at a concentration of about 5–50 nM and the test material can, if desired, be added at a series of dilutions. Typical incubations are 2–4 hr at about room temperature to 35° C., the time and temperature being interdependent.

After incubation, the solution containing the fibrinogen and test material is removed and the level of binding of fibrinogen measured by quantitating bound fibrinogen to GP IIb–IIIa. Any suitable means of detection may be used, but it is convenient to employ labeled fibrinogen, for example using radioactive, fluorescent or enzyme labels. Such methods are well known and need not be elaborated here.

Assessment of the results is aided by employing a control sample, usually identical to the test sample except that the test substance is absent. In this case, percent inhibition may be calculated using the amount of Fg bound in the control as representing the basis, so that $$\% \text{ inhibition} = \frac{\text{control} - \text{test}}{\text{control}} \times 100.$$

Other measures of inhibition effectiveness, such as $IC_{50}$, may also be used.

The assay systems of the invention further include characterization of the PAI specificity by binding inhibition assays identical to that above but substituting other adhesive proteins for Fg and other receptors for GP IIb–IIIa. In particular, inhibition of Vn/VnR; Fn/FnR; Fn/GP IIb–IIIa and vWF/GP IIb–IIIa binding may be assessed. The adhesive protein and receptors for these assays are available in the art.

Administration and Utility

The PAIs of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts ∂extracorporeal circulating devices"). These syndromes represent a variety of stenotic and occlusive vascular disorders thought to be initiated by platelet activation on vessel walls.

The PAIs may be used for prevention or abortion of arterial thrombus formation, in unstable angina and arterial emboli or thrombosis, as well as treatment or prevention of myocardial infarction (MI) and mural thrombus formation post MI. For brain-related disorders, treatment or prevention of transient ischemic attack and treatment of thrombotic stroke or stroke-in-evolution are included.

The PAIs may also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention may be used in numerous nontherapeutic applications where inhibiting platelet aggregation is desired. For example, improved platelet and whole blood storage can be obtained by adding sufficient quantities of the peptides, the amount of which will vary depending upon the length of proposed storage time, the conditions of storage, the ultimate use of the stored material, etc.

The PAI dosage can range broadly depending upon the desired affects and the therapeutic setting. Typically, dosages will be between about 0.01 and 10 mg/kg, preferably between about 0.01 to 0.1 mg/kg, body weight. Administration is preferably parenteral, such as intravenous on a daily basis for up to a week or as much as one or two months or more, all of which will vary with the peptide's size. If the peptides are sufficiently small (e.g., less than about 8–10 amino acid residues) other routes of administration can be utilized, such as intranasally, sublingually, or the like.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

EXAMPLE 1

Assay for Snake Venom Platelet Adhesion Inhibitors

A. Description of Assays

Purified platelet GP IIb–IIIa receptor was prepared as described by Fitzgerald, L. A., et al., *Anal Biochem* (1985) 151:169–177. Vitronectin receptor was prepared as described by Smith, J. W., *J Biol Chem* (1988) 263:18726–18731. After purification, the receptors were stored in 0.1% Triton X-100 at 0.1–1.0 mg/ml.

The receptors were added to 96-well flat-bottom ELISA plates (Linbro EIA-Plus microtiter plate, Flow Laboratories) by diluting 1:200 with a solution of 20 mM Tris-HCl, 150 mM NaCl, 1 mM CaCl$_2$, pH 7.4, to reduce the Triton X-100 concentration to below its critical micellar concentration and adding an aliquot of 100 ul to each well. The wells were all allowed to incubate overnight at 4° C., and then aspirated to dryness. Nonspecific binding was blocked by the addition of bovine serum albumin (BSA) at 35 mg/ml in the above buffer for 2 hr at 30° C. The wells were then washed once with binding buffer (50 nM Tris-HCl, 100 mM NaCl, 2 mM CaCl$_2$, 1 mg/ml BSA).

The corresponding ligands (fibrinogen, von Willebrand Factor, or vitronectin) were labeled with $^{125}$I or conjugated to biotin using commercially available reagents and standard protocols. The labeled ligands were added to the receptor-coated wells at final concentration of 10 nM (100 ul/well) and incubated for 3 h at 30° C. in the presence or absence of the test samples. After incubation, the wells are aspirated to dryness and bound ligand is quantitated.

For $^{125}$I-labeled ligands, the protein is solubilized with 250 ul SDS. For biotinylated ligands, the bound protein is detected by the addition of antibiotin antibody conjugated to alkaline phosphatase followed by addition of substrate (p-nitrophenyl phosphate), and determination of the optical density of each well at 405 nm. Decreased color development or decreased $^{125}$I content is observed in wells incubated with test samples which inhibit binding of ligand to receptor.

B. Determination of Adhesion Inhibition in Crude Venom

Sixty-eight crude, lyophilized snake venoms obtained from either Sigma Chemical Company (St. Louis, Mo.) or Miami Serpentarium Labs (Salt Lake City, Utah) were dissolved at 1 mg/ml in buffer (50 mM Tris, 100 mM NaCl, 0.02% azide, 2 mM CaCl$_2$). One ml aliquots of the solutions were subjected to ultrafiltration through Centrocon-10 (YM membrane) microconcentrators (Amicon, Danvers, Mass.). The filtrates were used as test samples in the receptor/ligand assay of paragraph A using the GP IIb–IIIa/fibrinogen system, and detecting binding using biotinylated fibrinogen. The results are shown in Table 1.

TABLE 1

| CENTRICON 10 PURIFIED VENOMS SCREENED IN IIb–IIIa PLATE ASSAY | |
|---|---|
| | Activity |
| Elapids | |
| *Austrelaps superba* (Australian Copperhead) | — |
| *Acanthopis antarcticus* (Death Adder) | — |
| *Dendroaspis jamesonii* (Jameson's Mamba) | — |
| *Notechis scutatus* (Mainland Tiger) | — |
| *Pseudechis colleti guttatus* (Blue-bellied) | — |
| *Pseudechis textillis textillis* (Common Brown) | — |
| *oxyuranus scutellatus* (Papuan Taipan) | — |
| Viperinae (True Vipers) | |
| *Atheris squamigera* (Green Bush Viper) | — |
| *Bitis nasicornus* (River Jack) | — |
| *Causus rhombeatus* (Rhombic Night Adder) | — |
| *Cerastes cerastes* (Desert Horned Viper) | — |
| *Cerastes vipera* (Sahara Horned Viper) | — |
| *Echis carinatus* (Saw-scaled Viper) | + |
| *Echis colorata* (Carpet Viper) | + |
| *Eristicophis macmahonii* (Macmahons Viper) | ++ |
| *Pseudocerastes fieldi* (Persian Horned Viper) | — |
| *Vipera xanthina xanthina* (Ottomans Viper) | — |
| *Vipera ammodytes* (Long-nosed Viper) | — |
| *Vipera r. russelli* (Russells Viper) | — |
| *Vipera r. siamensis* | — |
| *Vipera palaestinae* (Palestine Viper) | — |
| Crotalinae (Pit Vipers) | |
| *Agkistrodon rhodostoma* (Malayan Pit Viper) | + |
| *Agkistrodon halys blomhoffi* (Mamushi) | + |
| *Agkistrodon hypnale* (Hump-nosed Viper) | + |
| *Agkistrodon acutus* (Sharp-nosed Viper) | ++ |
| *Agkistrodon bilineatus* (Mexican Moccasin) | — |

TABLE 1-continued
CENTRICON 10 PURIFIED VENOMS SCREENED IN IIb-IIIa PLATE ASSAY

| | Activity |
|---|---|
| *Agkistrodon contortrix contortrix* | − |
| *Agkistrodon c. laticinctus* | − |
| *Agkistrodon c. pictigaster* | − |
| *Agkistrodon contortrix mokasen* (Northern Copperhead) | − |
| *Agkistrodon piscivorous piscivorous* (Eastern Cottonmouth) | − |
| *Agkistrodon piscivorus leucostoma* (Western Cottonmouth) | + |
| *Agkistrodon piscivorous conanti* | + |
| *Bothrops asper* | + |
| *Bothrops nummifer* (Jumping Viper) | − |
| *Bothrops cotiara* (Cotiara) | + |
| *Bothrops jararacussu* (Jararacussu) | + |
| *Bothrops jararaca* (Jararaca) | + |
| *Bothrops lansbergi* | + |
| *Bothrops alternata* (Urutu) | − |
| *Bothrops medusa* | + |
| *Bothrops neuwiedi* | + |
| *Bothrops nasuta* | + |
| *Bothrops pradoi* | + |
| *Bothrops schlegli* (Schlegels Viper) | + |
| *Trimeresurus gramineus* (Formosan Green Habu) | + |
| *Trimeresurus flavoviridis* (Okinawa Habu) | + |
| *Trimeresurus wagleri* | − |
| *Lachesis mutas* (Bushmaster) | + |
| *Crotalus durrisus terrificus* (Tropical Rattlesnake) | − |
| *Crotalus scutalatus* (Mojave rattlesnake) | − |
| *Cortalus horridus horridus* (Timber Rattlesnake) | + |
| *Crotalus horridus atricaudatus* (Canebrake RS) | − |
| *Crotalus atrox* (Western Diamondback) | + |
| *Crotalus adamanteus* (Eastern Diamondback) | − |
| *Crotalus basilicus* (Mexican West-coast RS) | + |
| *Crotalus molossus molossus* (Black-tailed RS) | + |
| *Crotalus ruber ruber* (Red diamondback RS) | + |
| *Crotalus cerastes cerastes* (Mojave sidewinder) | + |
| *Crotalus viridis viridis* (Prairie Rattlesnake) | + |
| *Crotalus v. helleri* (Southern pacific RS) | + |
| *Crotalus v. oreganus* (Northern pacific RS) | + |
| *Crotalus v. cereberus* (Arizona black RS) | + |
| *Crotalus v. lutosus* (Gret Basin RS) | + |
| *Crotalus v. concolor* (Midget-faded RS) | − |
| *Sistrurus catenatus tergeminus* (Western massasauga) | + |
| *Sistrurus milarius barbouri* (Southeastern Pigmy Rattlesnake) | + |

It is seen that the activity is present in some, but not all, species of Viperinae, but absent in all species tested of Elapidae.

FIG. 1 shows the results at various dilutions of the filtrate for four species. Even at the greatest dilution, 25 ul/0.5 ml, tile three active venoms showed maximal inhibition.

C. Specificity of Adhesion Inhibition

Figure 2A:
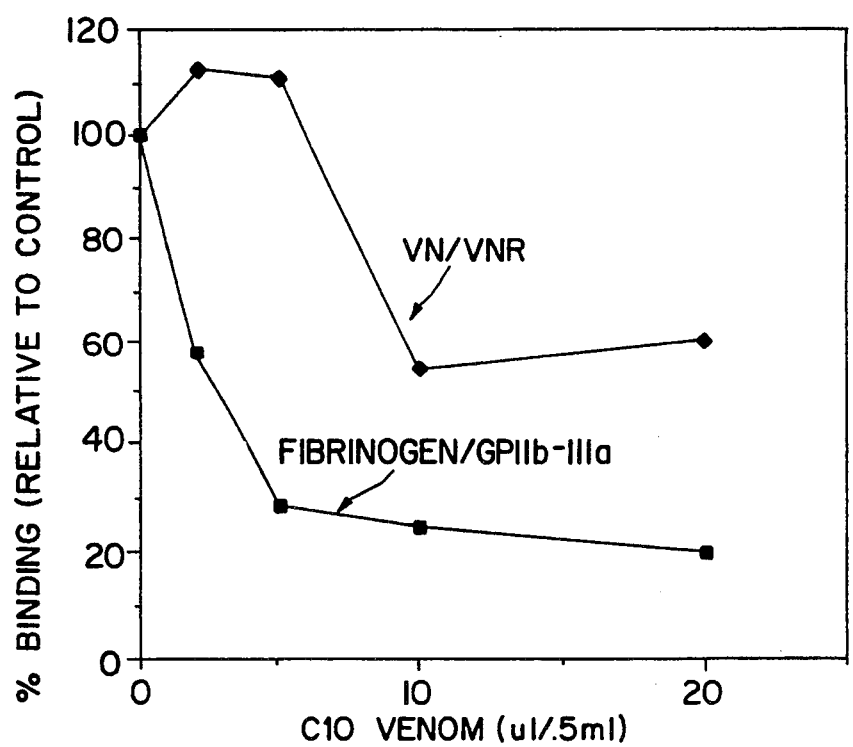
FIG. 2A, 2B and 2C show the dose-response adhesion inhibition of Centricon-10 ultrafiltrates of crude venoms in both fibrinogen/GP IIb-IIIa and vitronectin/vitronectin receptor assays to show purified PAI from *Sistrurus milarus barbouri.*
Figure 2B:
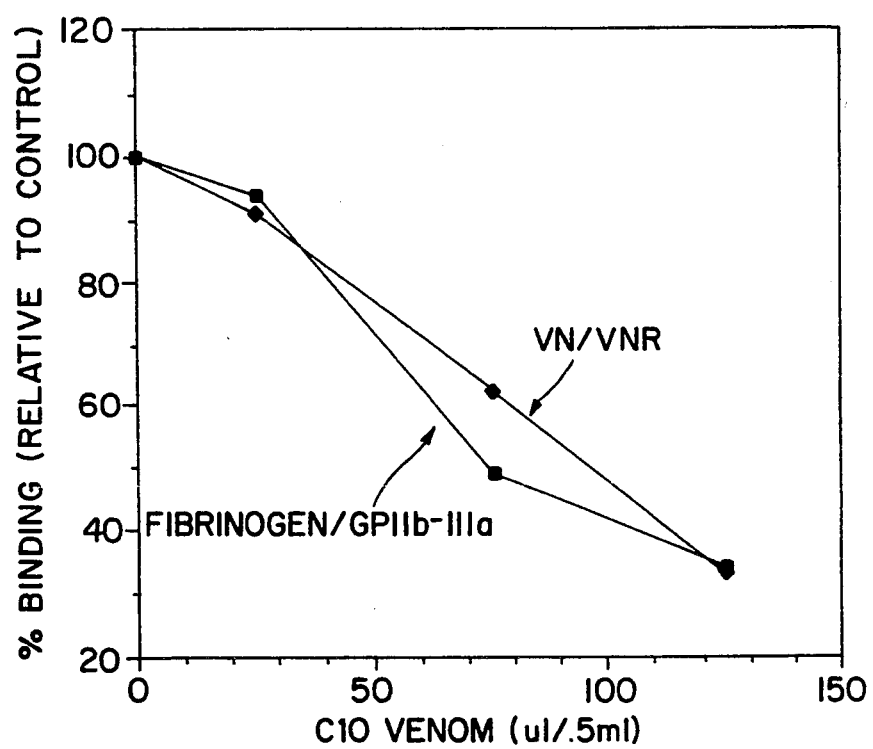
Figure 2C:
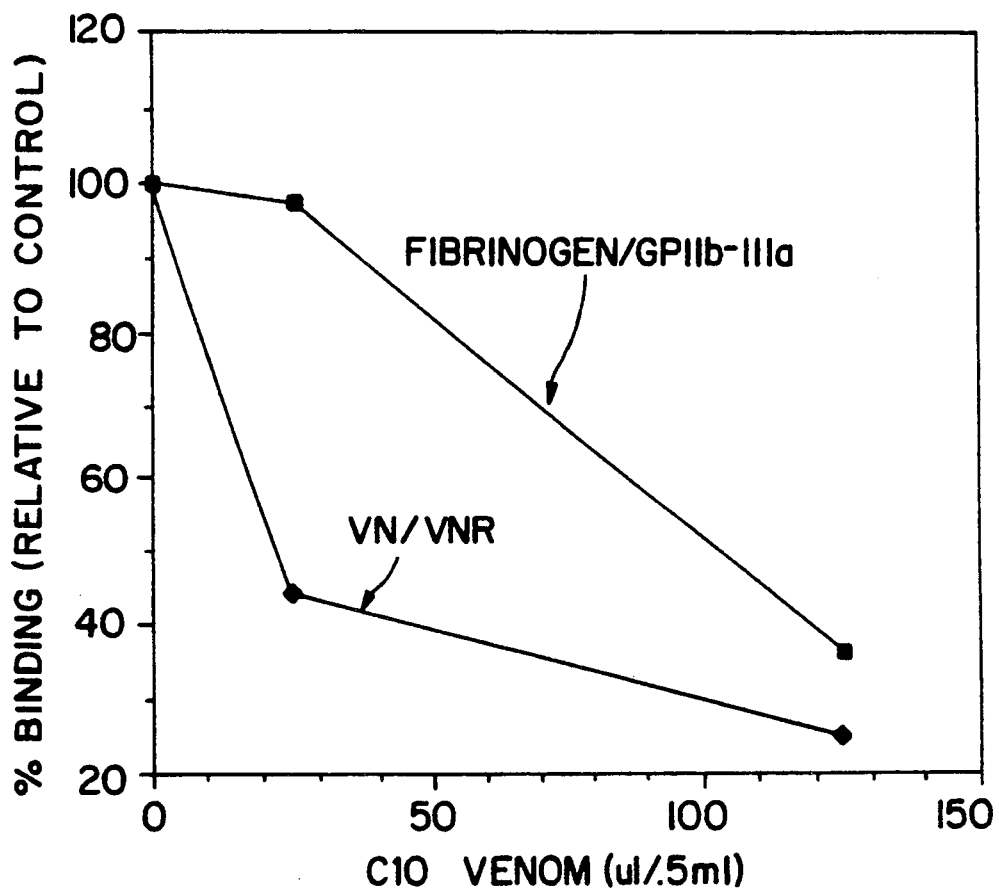

Ultrafiltrates from three species of snake venom, *Sistrurus m. barbouri*, *Crotalus ruber ruber*, and *Crotalus basilicus*, were tested in both the fibrinogen/GP IIb-IIIa and vitronectin/vitronectin receptor assays of paragraph A. The results were evaluated at various dilutions. As shown in FIG. 2A, the venom from *Sistrurus m. barbouri* preferentially inhibits the binding of fibrinogen to GP IIb-IIIa; as shown in FIG. 2B the venom of *Crotalus ruber ruber* inhibits binding in both systems approximately equally; and as shown in FIG. 2C the venom from *Crotalus basilicus* preferentially inhibits vitronectin/vitronectin receptor binding.

In the purifications described in Examples 2-6, PAI activity was assayed using a direct inhibition of platelet aggregation. Platelet rich plasm (PRP) was obtained from a healthy human volunteer. Aggregation was induced by the addition of 4 uM ADP to 0.5 ml PRP in an aggregometer (Chrono-log Corp.).

A table showing results of amino acid composition analysis of purified PAIs of Examples 2-6 will be found after Example 6.

This analysis was obtained by hydrolysis of peptides using 6 N HCl and analyzing the hydrolysate using a Beckman 121 HC analyzer equipped with a Model 126 data system. Cysteic acid was determined according to the method of Moore, *J Biol Chem* (1969) 230:235-237. Tryptophan was not determined.

EXAMPLE 2

Purification of Platelet Aggregation Inhibitor (PAI) From *Eristocophis macmahoni* Venom A solution of 45 mg of *Eristocophis macmahoni* venom (Miami Serpentarium Labs, Lot #EM23SZ) in 1.0 ml of 0.5% trifluoroacetic acid (TFA) was cooled on ice for 20 min, spun at 14,000 rpm for 3 min to remove insoluble material and loaded onto a 3.9 mm x 30 cm, C-18 Delta Pak reverse-phase HPLC column (Waters, Milford, Mass.) equilibrated with 5% acetonitrile containing 1% TFA. A gradient running from 5% to 15% acetonitrile over 5 min (2%/min) followed by a gradient from 15% to 30% acetonitrile over 35 min and then to 50% acetonitrile over 20 min, was run using a Waters 6000E liquid chromatograph. A flow rate of 1.5 ml/min was maintained throughout the gradient and column effluent was collected in 2 min fractions into polypropylene tubes.

The column effluent was monitored at 220 nm/2.5 absorbance units full scale (AUFS).

Fractions were concentrated to one-half their original volume using a Speed-Vac concentrator (Savant) followed by lyophilization. Samples were then reconstituted in 1 ml distilled water and aliquots (10-50 ul) assayed for their ability to inhibit human platelet aggregation in platelet-rich plasma induced by 20 uM ADP using a whole blood aggregometer (Chrono-Log Corp., Hayertown, Pa.).

Figure 3:
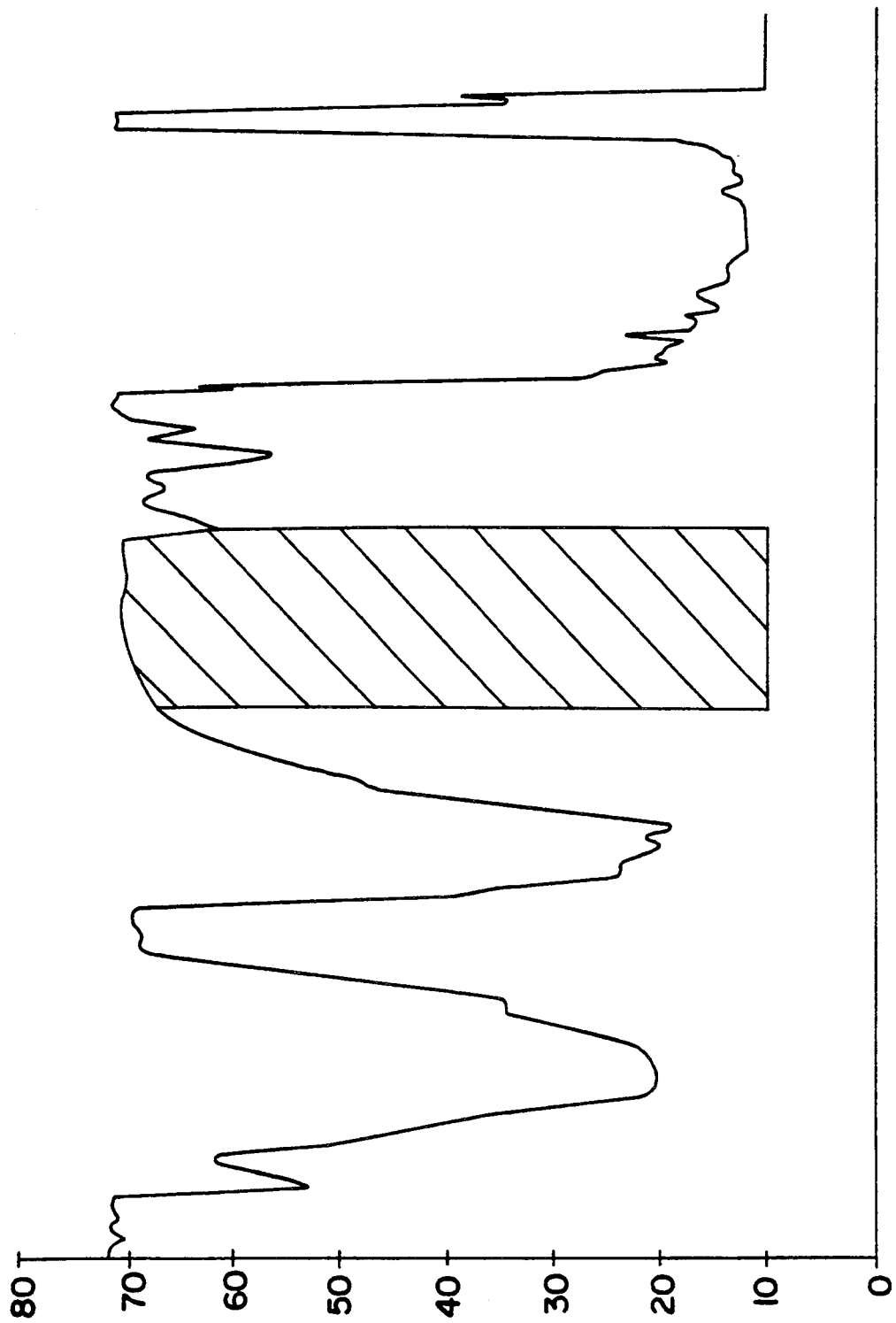
FIG. 3 shows the HPLC profile of crude PAI from *Eristicophis macmahoni* venom. The cross-hatched area contains the biologically active fractions.

As shown in FIG. 3, activity was found in fractions that eluted at 21-25% acetonitrile concentration. These fractions were then lyophilized and rerun on the C-18 HPLC column using shallower acetonitrile gradient as follows: Initial conditions consisted of 8% acetonitrile followed by a gradient to 25% acetonitrile over 68 min (0.25%/min), then to 60% acetonitrile in 10 min. One-minute fractions were collected, dried and reassayed for inhibitory activity in platelet aggregation of human platelets as above.

Figure 4:
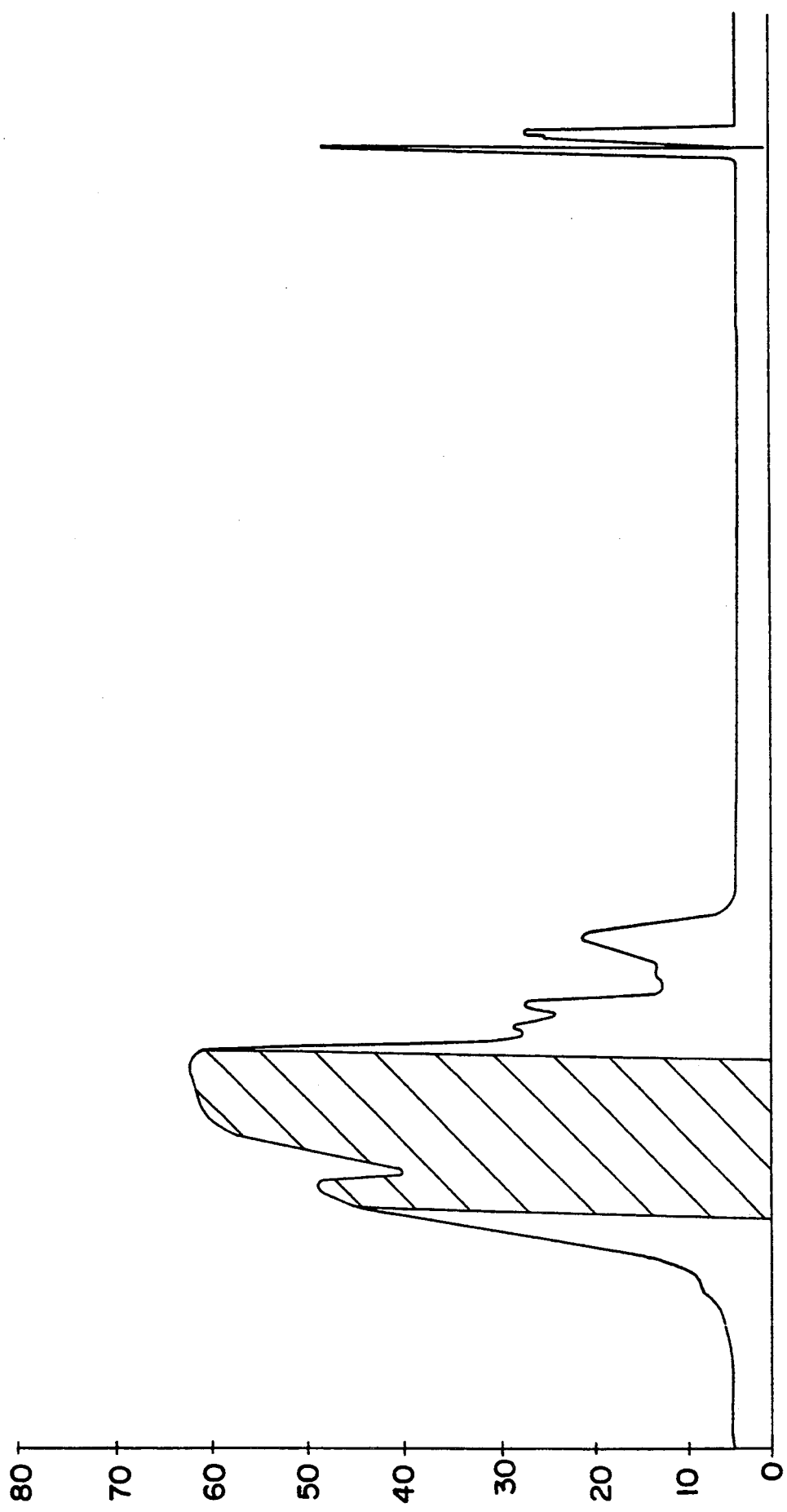
FIG. 4 shows the slow gradient HPLC profile of PAI fractions from FIG. 3.
Figure 5:
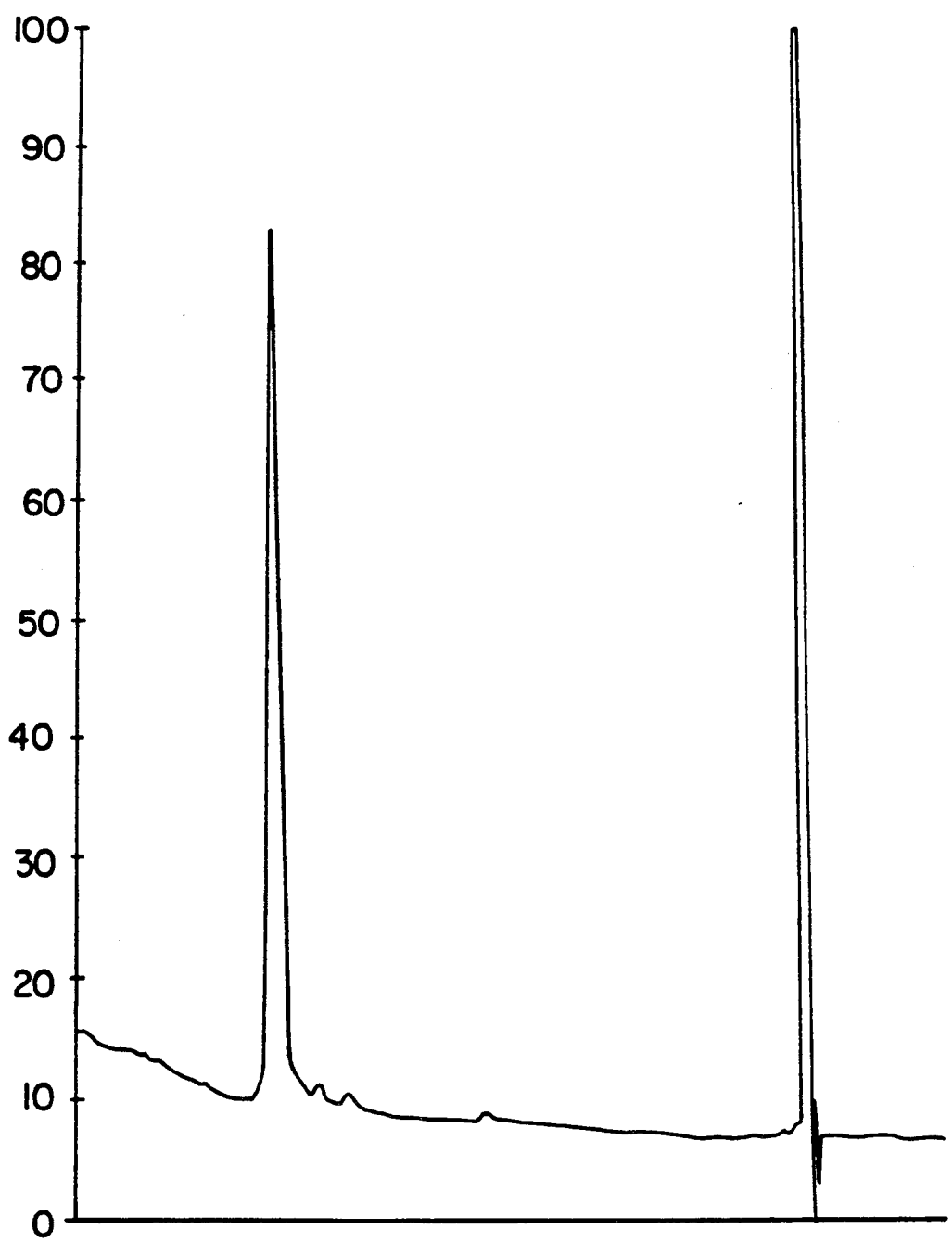
FIG. 5 shows the analytical HPLC profile of PAI fractions from FIG. 4 to demonstrate purified PAI from *Eristicophis macmahoni* venom.

As shown in FIG. 4, the activity eluted at 24% acetonitrile. The active fractions were then subjected to analytical HPLC with detection at 220 nm and eluted as a single symmetric bioactive component as shown in FIG. 5. Amino acid analysis of the HPLC-purified material showed that the peptide contains 49 residues including 7 cysteines, as set forth in Table 2.

EXAMPLE 3

Purification of PAI from *Sistrurus catenatus tergeminus* Venom

Three hundred sixty mg of *Sistrurus c. tergeminus* venom (Miami Serpentarium Labs, Lot #ST6SZ) was dissolved in 7.0 ml of 0.5M acetic acid and applied to a column of Sephadex G-50 fine (Pharmacia, 2.5×100 cm) equilibrated and eluted with 0.5M acetic acid. The column was run at a flow rate of approximately 25 ml/hr and 5-ml fractions collected. Twenty-five ul of each fraction was pooled in groups of 10 fractions (i.e., fractions 1-10, 11∝20, etc.) and lyophilized for analysis. The dried pooled fractions were redissolved in water and aliquots assayed for inhibitory activity in ADP-stimulated aggregation of human platelets. Active fractions (31-40) were pooled and lyophilized.

This material was dissolved in 2 ml of 0.5% TFA and loaded onto a 19 mm×30 cm C-18 Delta Pak reverse-phase HPLC column (Waters) equilibrated with 8% acetonitrile containing 0.1% TFA. A gradient from 8% to 30% acetonitrile concentration over 30 min and then to 60% acetonitrile over twenty min was run at a flow rate of 18 ml/min. The column effluent was collected into polypropylene tubes in 0.2 min fractions and monitored at 220 nm/2.2 AUFS. Fractions were concentrated on a Speed-Vac concentrator (Savant), lyophilized and assayed for antiaggregation activity with human platelets as previously described.

Figure 6:
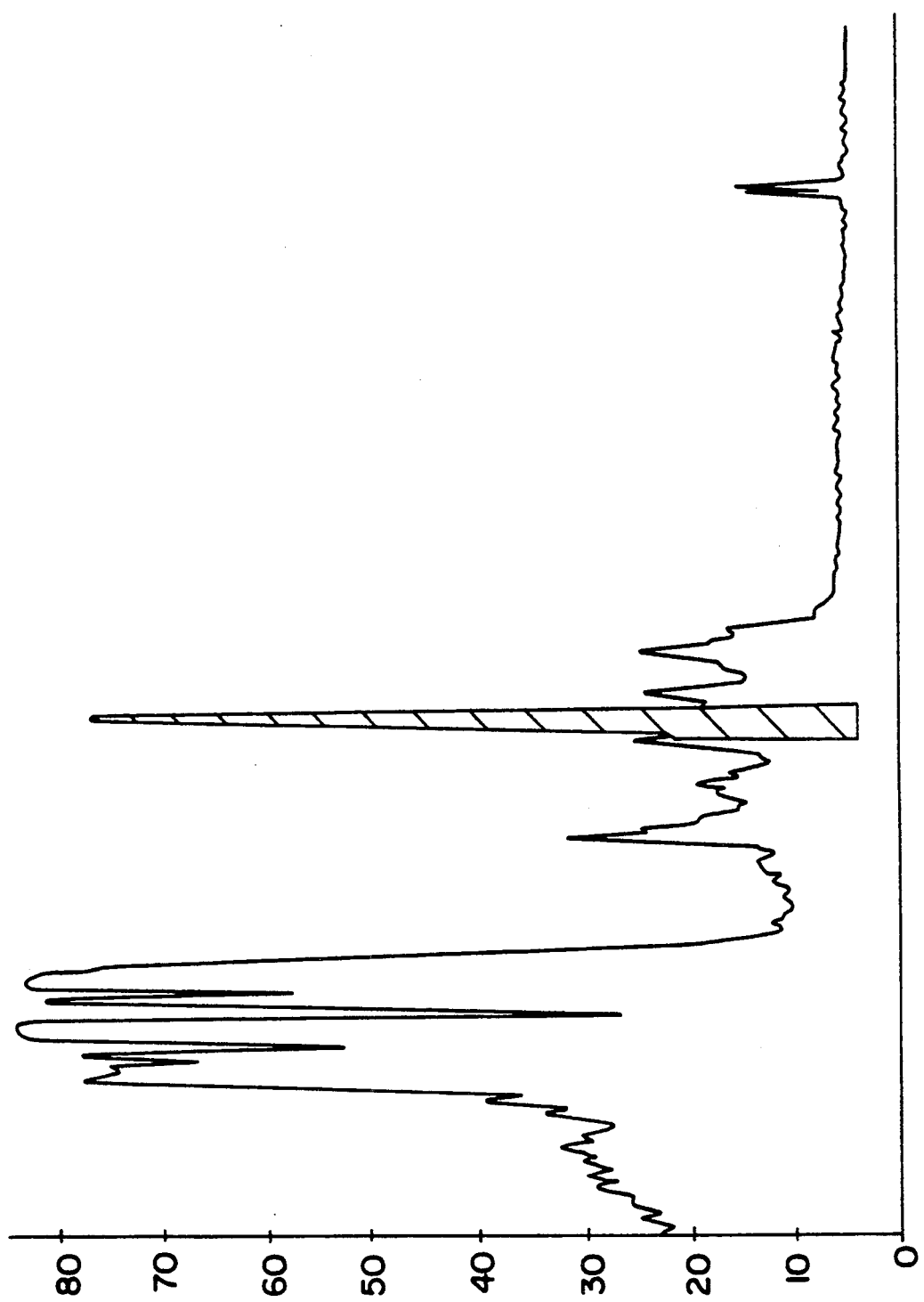
FIG. 6 depicts the HPLC profile of PAI obtained from G-50 fractions of crude *Sistrurus c. tergeminus* venom. The cross-hatched area contains the bioactive fractions.
Figure 7:
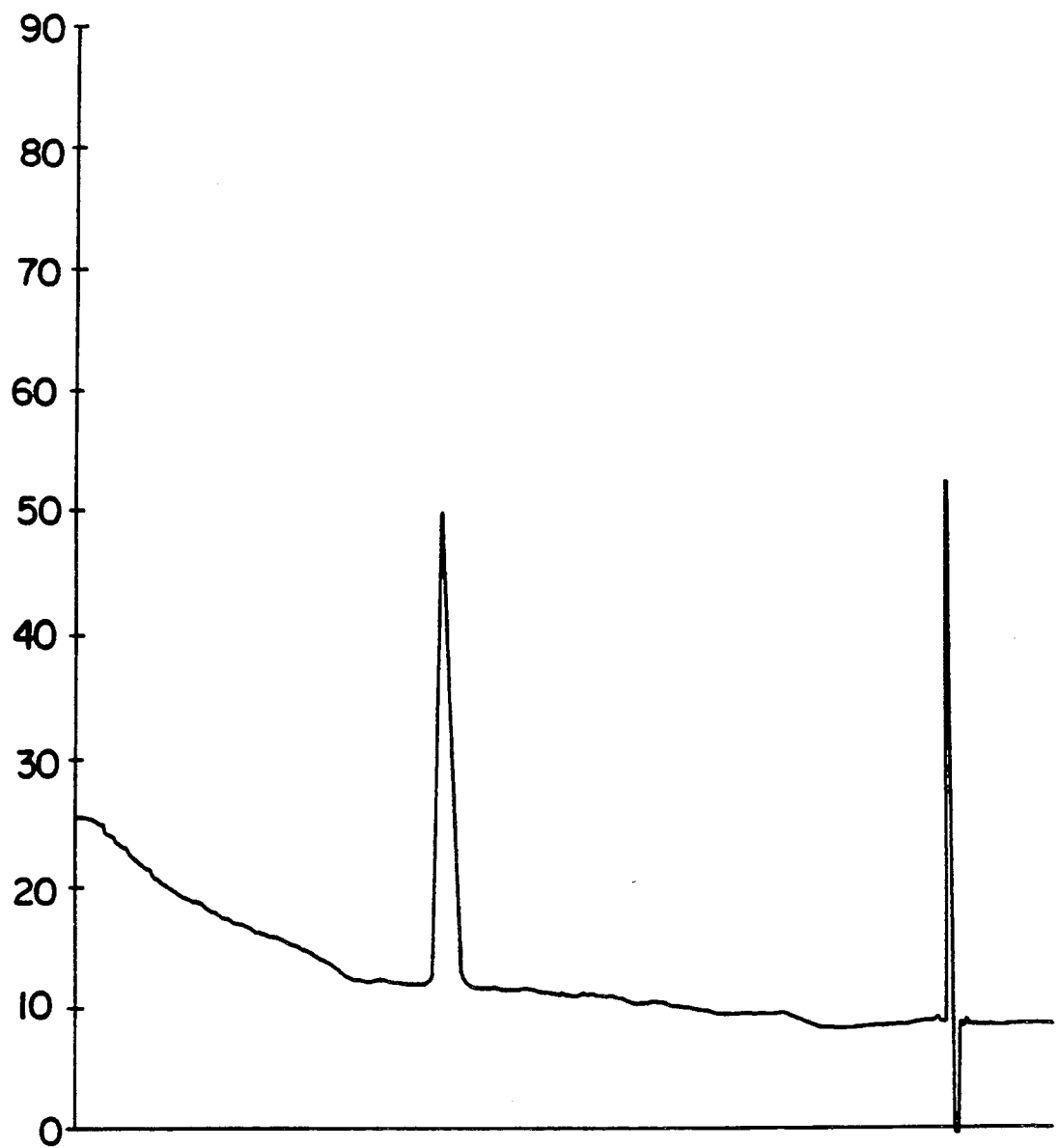
FIG. 7 depicts the HPLC profile of PAI fractions from FIG. 6 to show purified PAI from *Sistrurus milarus tergeminus.*

FIG. 6 shows that the PAI-containing fraction elutes at 24-25% acetonitrile. Analysis of these active fractions using HPLC with detection at 220 nm showed a symmetric bioactive component, as shown in FIG. 7. The amino acid analysis of this material showed a peptide of 71-72 residues, including 12 cysteines, as shown in Table 2.

A portion of the purified peptide was reduced and alkylated with iodoacetamide and purified on a C-18 reverse-phase HPLC column. N-terminal sequence analysis of this material revealed the following amino acid sequence for 23 cycles of Edman degradation: Glu-Ala-Gly -Glu-Glu-Cys-Asp-Cys-Gly-Ser-Pro-Ala-Asn-Pro-Cys-Cys-Asp -Ala-Ala-Thr-Cys-Lys-Leu.

Figure 8:
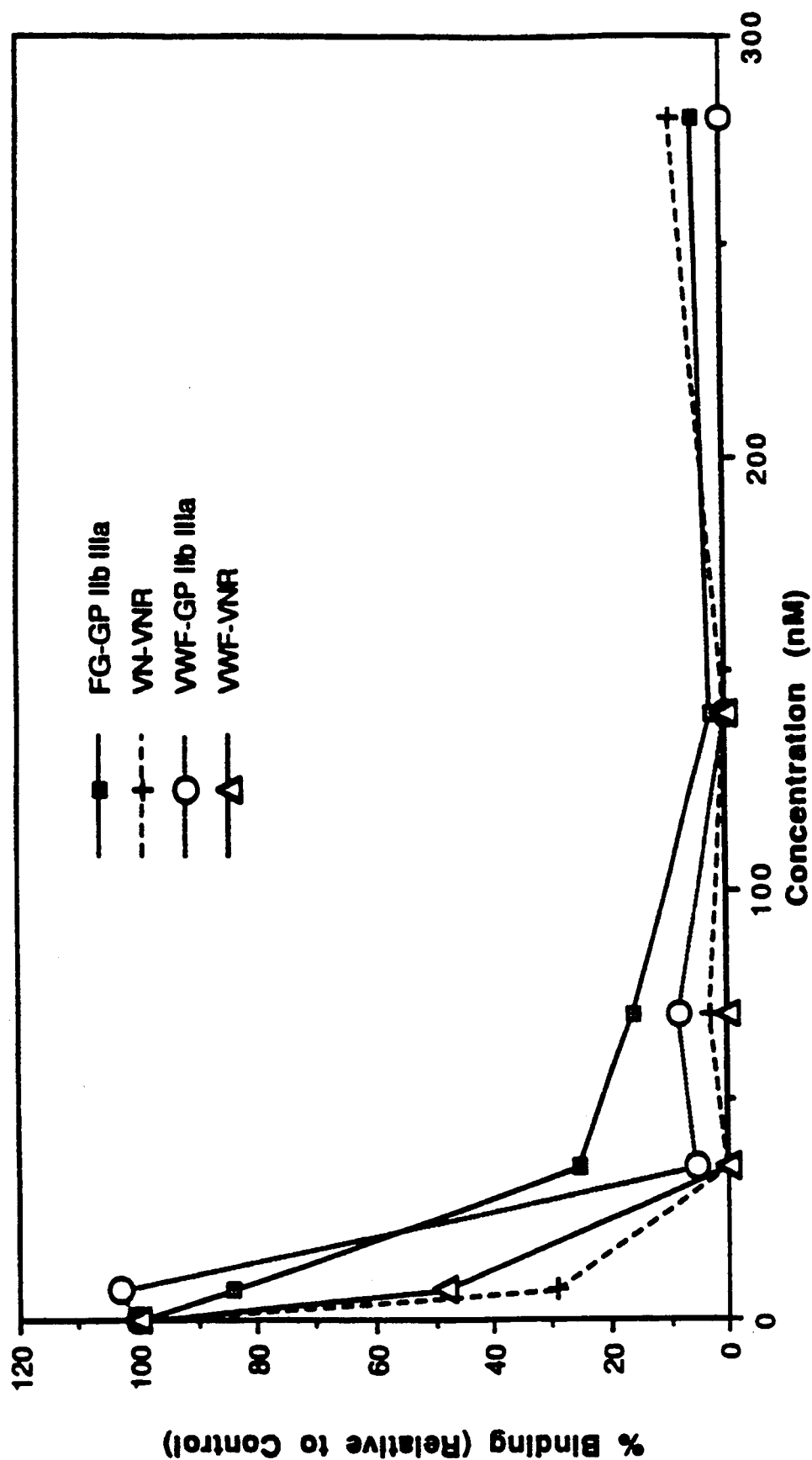
FIG. 8 shows the activity of the purified tergeminin PAI of FIG. 7 in inhibiting binding in several receptor assays.

The purified peptide was tested in the receptor-based assays described in Example 1, paragraph A. Concentrations of pure peptide at less than 100 nM inhibited the binding of Fg and vWF to GP IIb-IIIa and of Vn and vWF to the vitronectin receptor, as shown in FIG. 8.

EXAMPLE 4

Purification of Platelet Aggregation Inhibitor from *Sistrurus milarus barbouri* Venom Two hundred mg of *Sistrurus m. barbouri* venom (Miami Serpentarium Labs, Lot #SM13SZ) was dissolved in 7.0 ml of 0.5M acetic acid and applied to a column of Sephadex G-50 fine (Pharmacia, 2.5×100 cm) equilibrated and eluted with 0.5M acetic acid. The column was run at a flow rate of 26 ml/hr and 5 ml fractions were collected and analyzed for antiplatelet aggregation activity as previously described. Active fractions (41-50) were pooled and lyophilized. This material was redissolved in 2.0 ml 0.5% TFA and loaded onto the preparative C-18 HPLC column as in Example 3 and eluted employing the same gradient conditions. Two-tenths-min fractions from the column were collected into polypropylene tubes, concentrated, lyophilized and analyzed for platelet aggregation inhibitory activity.

Figure 9:
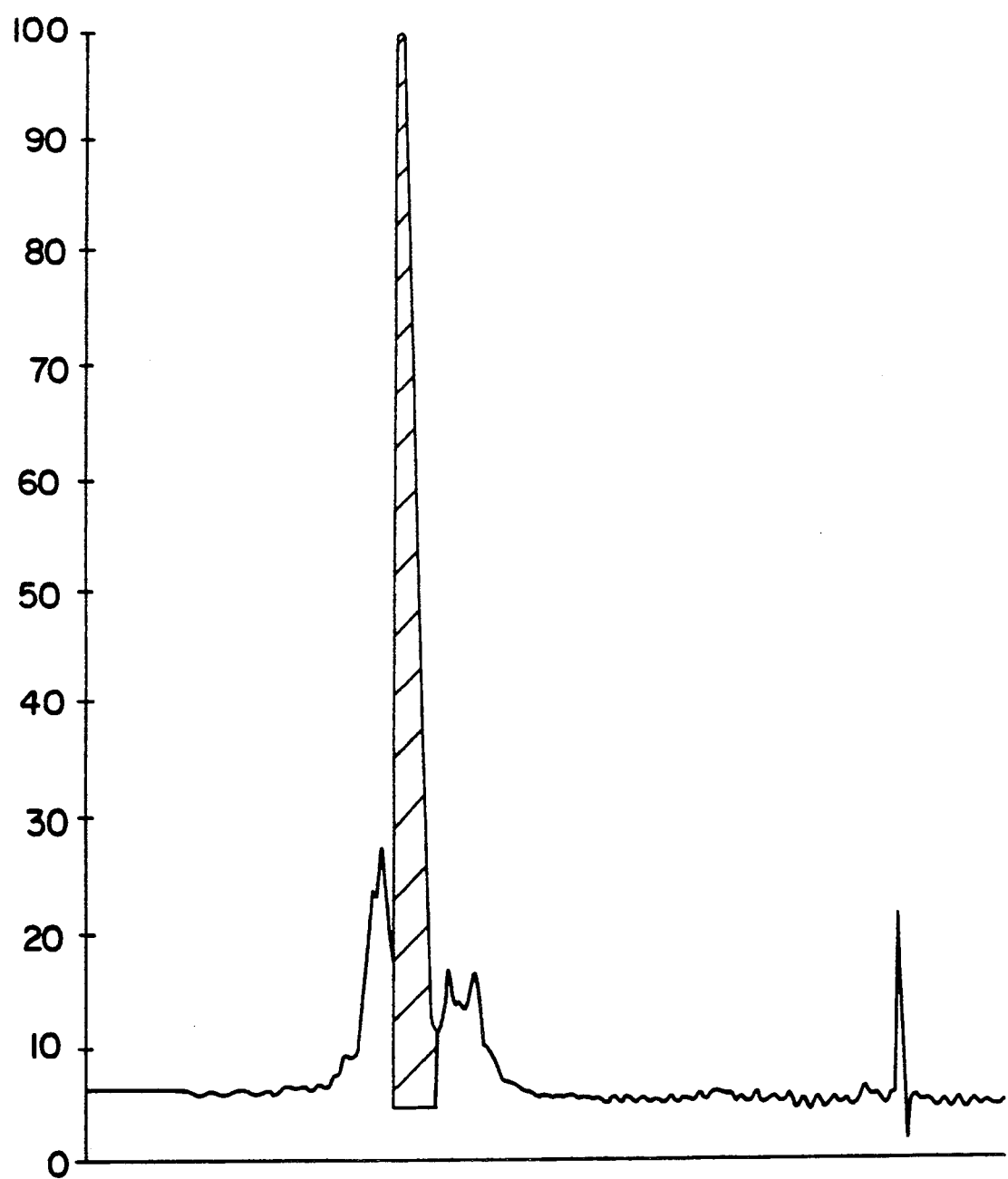
FIG. 9 depicts the HPLC profile of platelet aggregation inhibitor obtained from G-50 fractions of crude *Sistrurus m. barbouri* venom. The cross-hatched areas contain the bioactive fractions.
Figure 10:
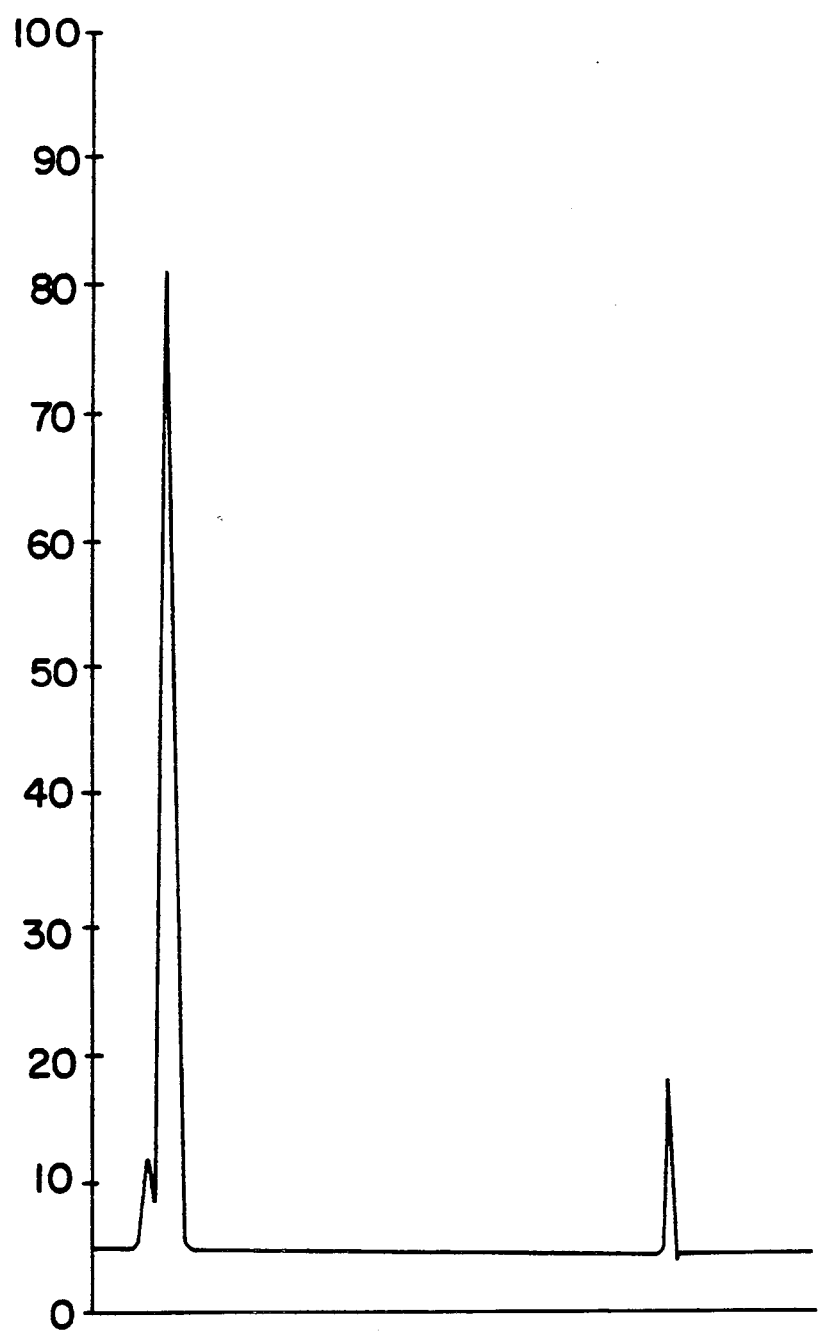
FIG. 10 depicts the HPLC profile of active PAI fractions of FIG. 9 to show purified PAI from *Sistrurus milarus barbouri.*

FIG. 9 shows the activity profile from this HPLC column. The active fractions were subjected to analytical HPLC, which showed several fractions (45-47) which were more than 90% homogeneous. The peptide of fraction 46 (150 ug) was purified to homogeneity on an analytical C-18 column with manual collection of the symmetric peak, as shown in FIG. 10. Amino acid analysis of this material showed a peptide of 71-72 amino acids, including 12 cysteine residues, as set forth in Table 2.

The purified peptide (150 ug) was dissolved in 300 ul reaction buffer (6M guanidine HCl, 0.25M Tris-HCl, 20 mM EDTA, 20 mM dithiothreitol (DTT), pH 7.5) for 1.5 hours at room temperature to reduce the peptide. This was followed by reaction of 3 ul of 4-vinylpyridine (Aldrich) at room temperature for an additional hour. The reaction was stopped by addition of 200 ul 1% TFA and loaded onto an analytical C-18 HPLC column and eluted with an acetonitrile gradient in water containing 0.1% TFA, starting at 8% acetonitrile and running to 25% acetonitrile in 20 minutes, then to 60% acetonitrile in 10 minutes.

A portion of this pyridylethylated material was submitted to N-terminal sequence analysis, as described above, and exhaustive proteolytic cleavage of the reduced and alkylated peptide was performed using endoproteinase Lys-C and endoproteinase Asp-N with peptide fragments isolated on either C-3 or C-18 reverse-phase HPLC columns using acetonitrile/water/TFA gradient elution. The amino acid sequence of the N-terminus of the intact peptide and isolated proteolytic fragments were determined as described by Yarden, Y., et al., Nature (1986) 323:226, using Edman degradation on a gas-phase sequencer.

The complete amino acid sequence of this isolated peptide, designated "barbourin" herein, is shown in FIG. 11, along with the sequences for the proteolytic fragments. A comparison of this sequence with those of other snake venom adhesion inhibitors is shown in FIG. 12.

EXAMPLE 5

Purification of PAI from *Lachesis mutas* venom 99 mg of *Lachesis mutas* venom (Miami Serpentarium Labs, Lot #LM15FZ) was dissolved in 2.0 ml of 0.5% trifluoroacetic acid was cooled on ice for 20 min, spun at 14,000 rpm for 3 min to remove insoluble material and loaded onto a 3.9 mm×30 cm, C-18 Delta Pak reversed-phase HPLC column (Waters) equilibrated with 5% acetonitrile containing 0.1% trifluoroacetic acid. A gradient form 5% to 15% acetonitrile over 5 min and then to 30% over 35 min (2%/min) and continued to 60% acetonitrile over 20 min was run. The flow rate was maintained at 1.5 ml/min and the column effluent monitored at 220 nm/3.0 AUFS. Two minute fractions were collected, concentrated by Speed-Vac and lyophilized. Fractions were assayed for platelet aggregation inhibitory activity.

Figure 13:
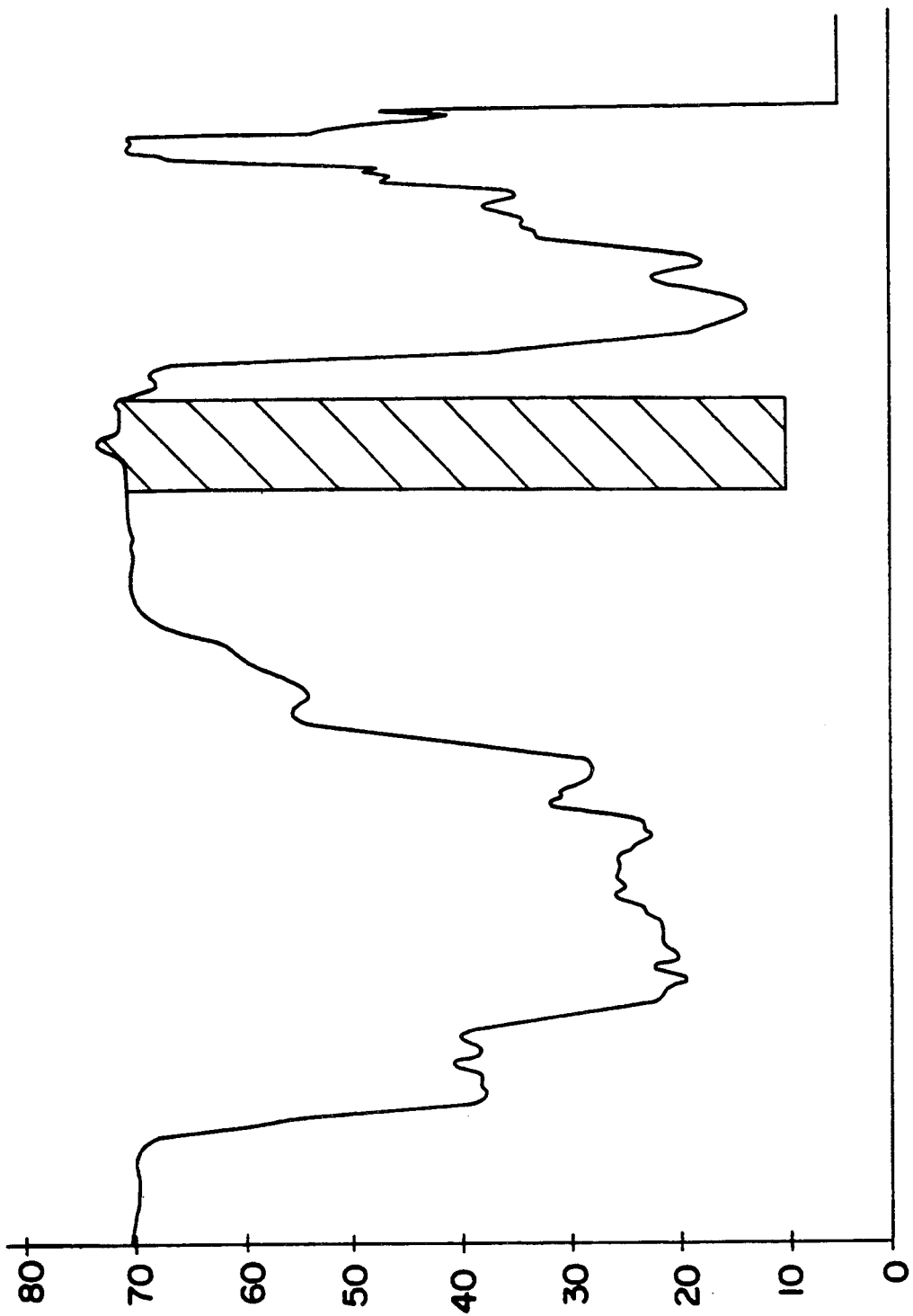
FIG. 13 depicts the HPLC profile of crude PAI from *Lachesis mutas* venom. Cross-hatched areas contain the biologically active fractions.
Figure 14:
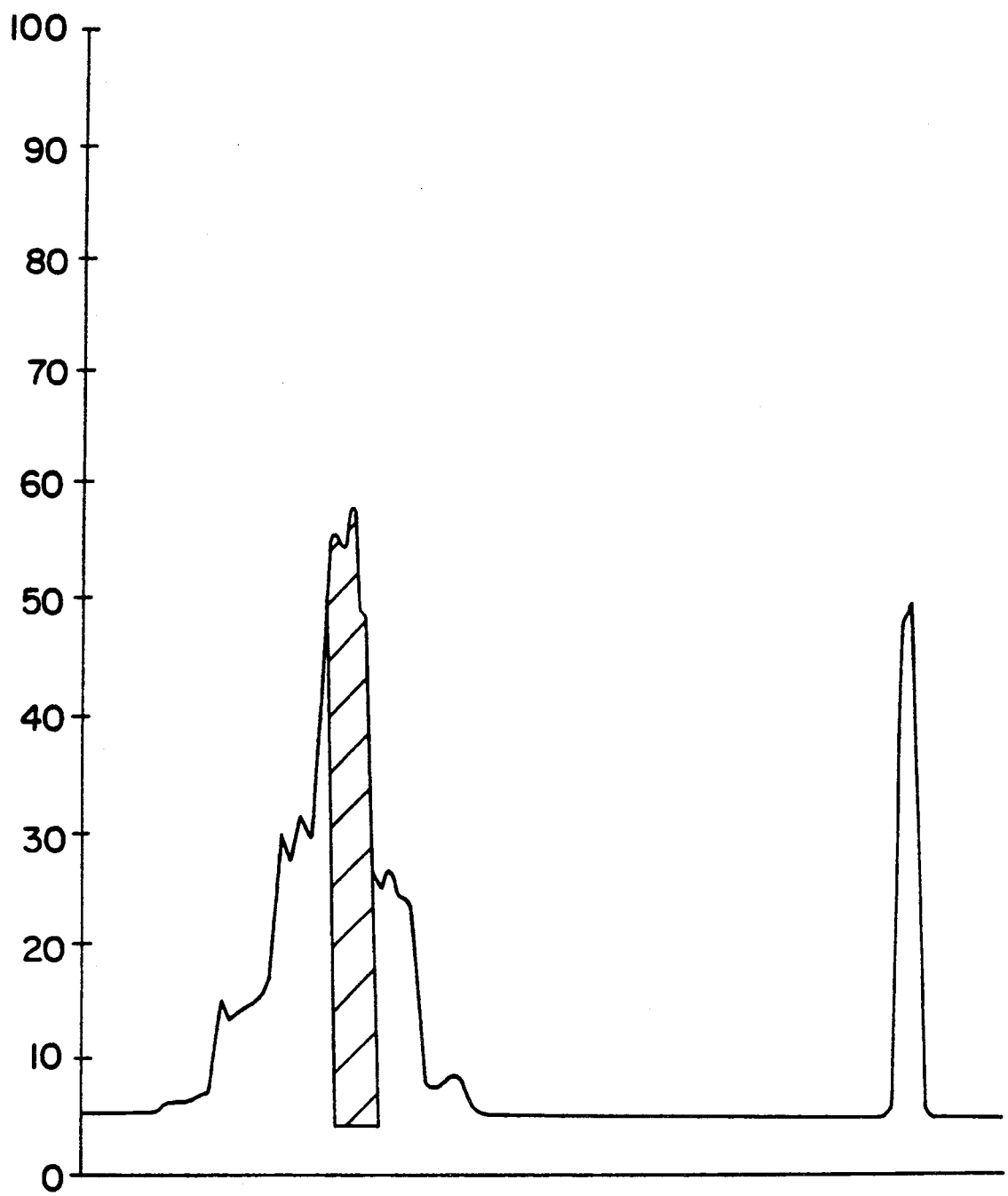
FIG. 14 depicts the slow gradient HPLC profile of the PAI active fractions from FIG. 13. Cross-hatched area contains the biologically active fractions.
Figure 15:
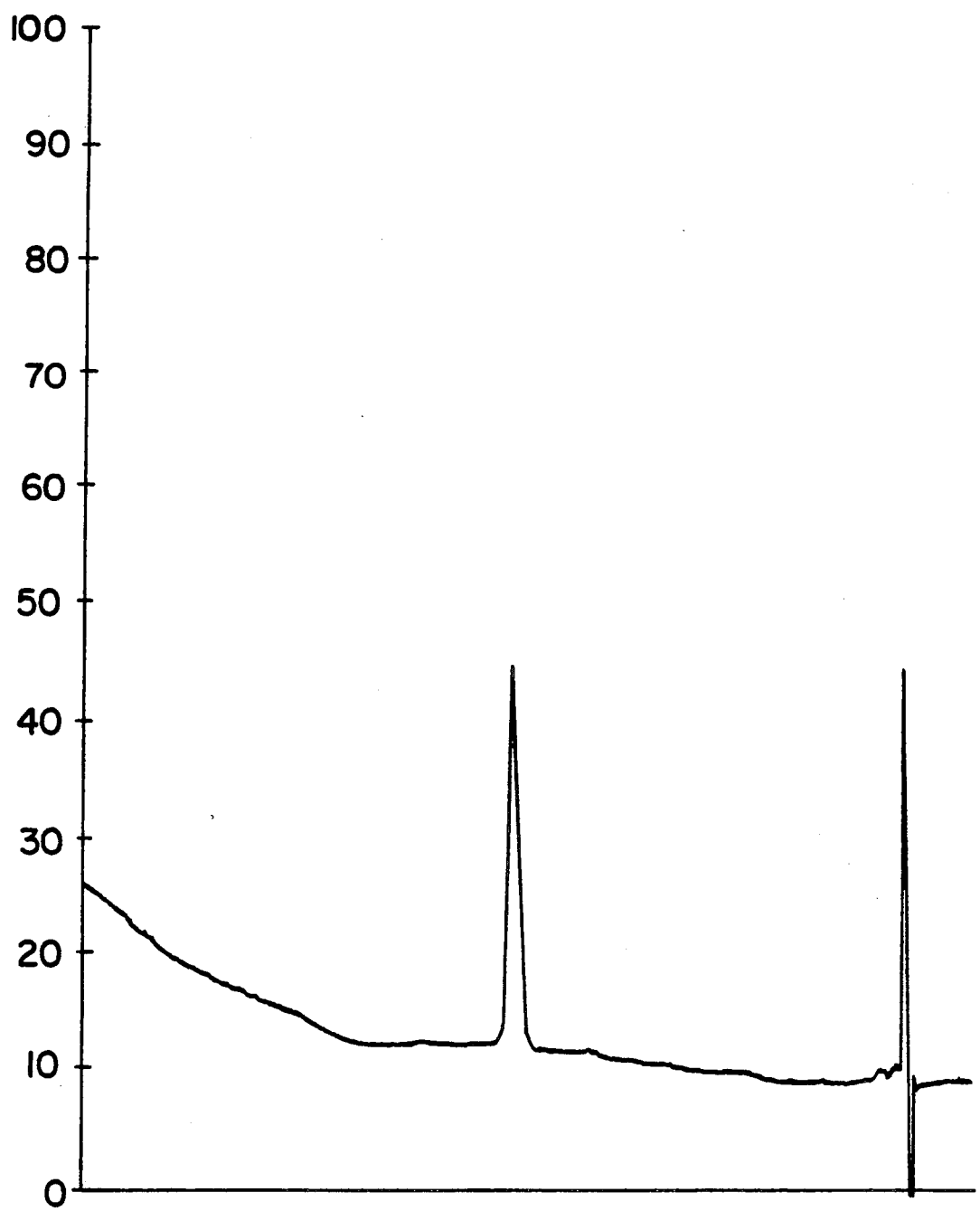
FIG. 15 depicts the analytical HPLC profile of PAI fractions of FIG. 14 to show purified PAI from *Lachesis mutas* venom.

FIG. 13 shows the active fractions which elute at 18% acetonitrile. These fractions were rerun on the C-18 column using a shallower gradient consisting of a 40 min gradient from 5-28% acetonitrile. One-min fractions were collected, concentrated, lyophilized and assayed for platelet aggregation inhibition activity, with the results shown in FIG. 14. These active fractions were run on an analytical C-18 column, and the eluted center peak fraction collected by hand. The eluted material, which is in a single symmetric peak, as shown in FIG. 15, was subjected to amino acid analysis and showed a peptide of 72-73 amino acids containing 12 cysteines, as shown in Table 2.

EXAMPLE 6

Purification of PAI from *Crotalus viridis viridis* venom 47 mg of *Crotalus viridis viridis* venom (Sigma Chemical Co., Lot #24F-0534) was dissolved in 1 ml of 0.5% trifluoroacetic acid, cooled on ice for 20 min, spun at 14,000 rpm for 3 min to remove insoluble material and loaded onto a 3.9 mm×30 cm C-18 Delta Pak reverse-phase HPLC column (Waters) equilibrated with 5% acetonitrile containing 0.1% trifluoroacetic acid. A gradient from 5% to 15% acetonitrile over 5 min (2%/min) followed by a gradient from 15% to 30% acetonitrile in 35 min and then to 60% acetonitrile in 60 min was run. A flow rate of 1.5 ml/min was maintained throughout the gradient and the column effluent was collected into polypropylene tubes in 2 min fractions. The column effluent was monitored at 220 nm/3.0 AUFS. Fractions were concentrated, lyophilized and assayed for platelet aggregation inhibitory activity.

Figure 16:
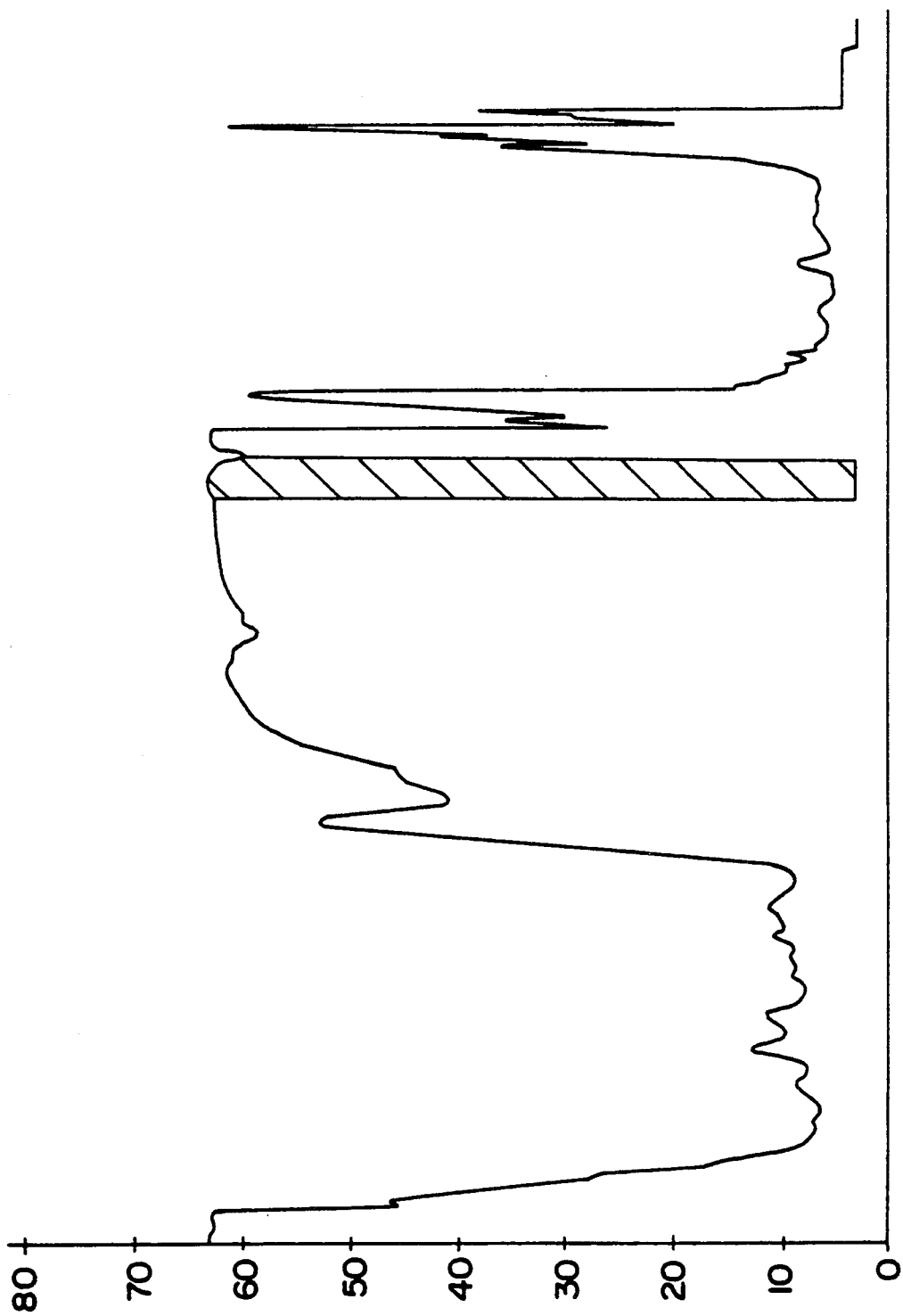
FIG. 16 depicts the HPLC profile of crude PAI from *Crotalus viridis viridis* venom. Cross-hatched area contains the biologically active fractions.
Figure 17:
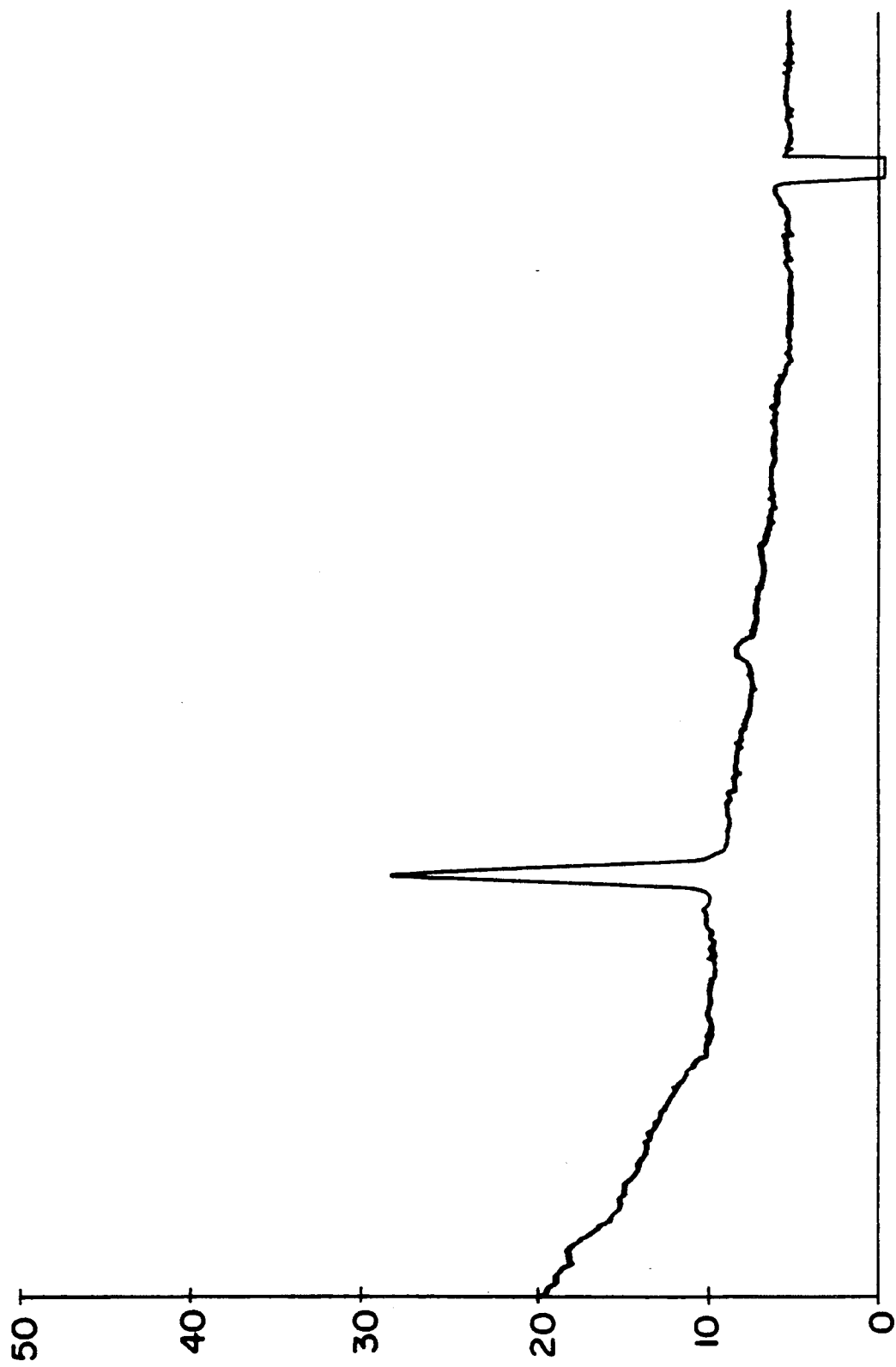
FIG. 17 depicts the HPLC profile of the PAI fractions of FIG. 16 to show purified PAI from *Crotalus viridis viridis* venom.
Figure 19A:
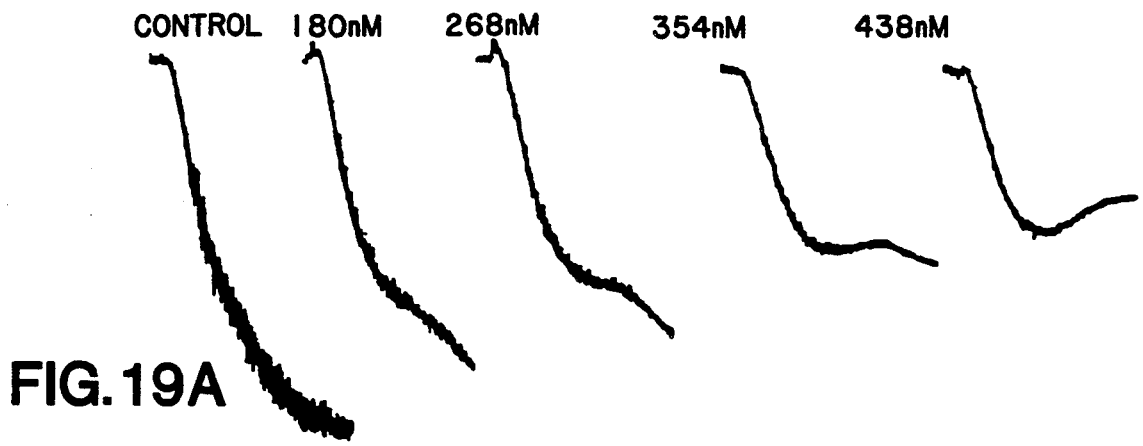
FIG. 19A, 19B and 19C show the dose-response effects of purified snake venom peptides to inhibit ADP (4 uM) induced human platelet aggregation in platelet rich plasma (PRP), as compared to echistatin.
Figure 19B:
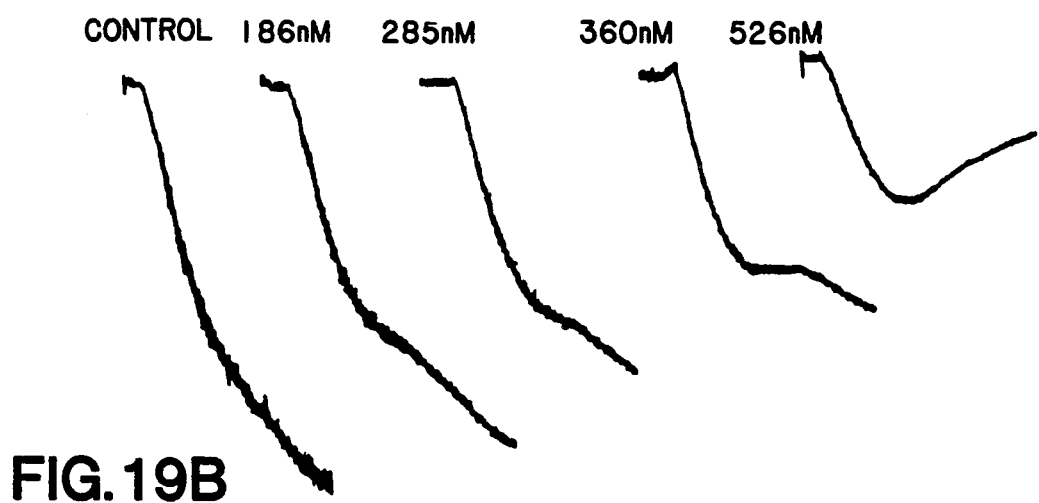
Figure 19C:
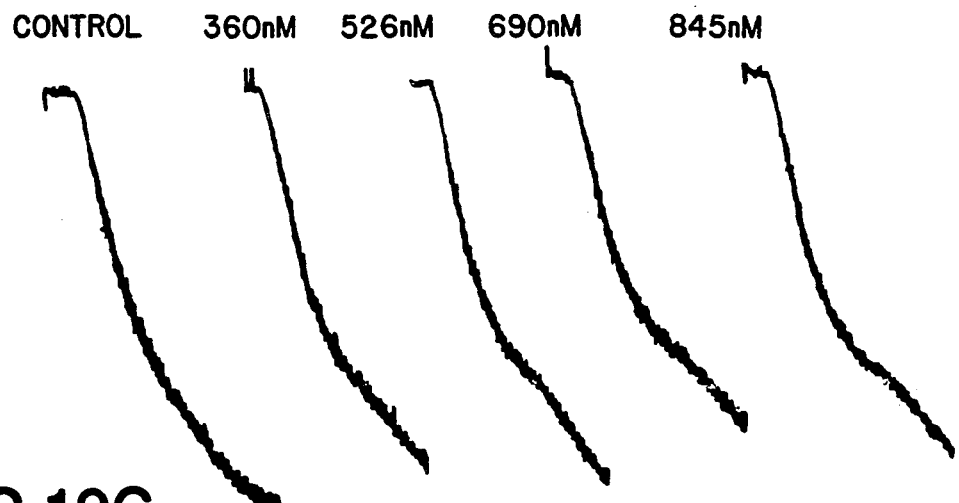

The active fractions, shown in FIG. 16 as 18–19% acetonitrile, were run on the C-18 HPLC column using a gradient of 8%–20% acetonitrile over 48 min (0.25%/min). The fractions were concentrated and lyophilized and tested for activity; the active fractions were run on a C-18 column using 8–16% acetonitrile over 10 min, 16–20% acetonitrile over 15 min, and then to 60% over 10 min. The effluent was monitored at 220 nm with individual peaks collected by hand into polypropylene tubes. Reanalysis of the active peak on analytical HPLC gave the results shown in FIG. 17. The amino acid analysis conducted on this peak showed a 74–75-residue peptide containing 12 cysteines, as set forth in Table 2.

trations (FIG. 19A, 19B, and 19C). Snake venom peptides from *Eristicophis macmahoni* and *Sistrurus m. barbouri* were at least twofold more potent than echistatin, in agreement with their order of potency observed for inhibiting fibrinogen binding to GP IIb-IIIa as presented above.

We claim:

1. A method for selecting a compound that selectively inhibits platelet aggregation over other cellular activities mediated by integrins, which method comprises:
   (a) contacting a sample of said compound with purified GP IIb-IIIa receptor coated onto a solid support in the presence of a solution of labeled fibrinogen or von Willebrand Factor under conditions wherein fibrinogen or von Willebrand factor binds to said GP IIb-IIIa;
   (b) measuring the binding of fibrinogen or von Willebrand factor to GP IIb-IIIa in comparison to the binding of fibrinogen or von Willebrand factor to GP IIb-IIIa in a control which does not contain said compound by measuring the amount of bound labeled fibrinogen;
   (c) determining the inhibition in (b);
   (d) contacting a sample of said compound with purified vitronectin receptor coated onto a solid support in the presence of a solution of labeled vitronectin under conditions wherein vitronectin binds to said vitronectin receptor;
   (e) measuring the binding of vitronectin to vitronectin receptor in comparison to the binding of vitronectin to vitronectin receptor in a control which does not contain said compound by measuring the

TABLE 2

| Amino acid | *Sistrurus m. barbouri* | *Sistrurus c. tergeminus* | *Lachesis mutas* | *Crotalus v. viridis* | *Eristicophis macmahoni* |
| --- | --- | --- | --- | --- | --- |
| Lys | 4 | 3 | 4 | 34 | 4 |
| His | 0 | 0 | 0–1 | 1 | 0 |
| Arg | 4 | 5 | 7 | 5 | 7 |
| Asx | 11 | 11 | 10 | 11 | 7 |
| Thr | 4 | 4 | 2 | 4 | 2 |
| Ser | 2 | 2 | 1 | 2 | 1 |
| Glx | 6–7 | 5–6 | 7 | 6 | 4 |
| Pro | 4 | 4 | 5 | 6 | 5 |
| Gly | 9 | 9 | 9 | 10 | 5 |
| Ala | 7 | 8 | 9 | 7 | 3 |
| Cys | 12 | 12 | 12 | 12 | 7 |
| Val | 2 | 2 | 0 | 1 | 2 |
| Met | 1 | 1 | 0 | 0 | 0 |
| Ile | 0 | 0 | 2 | 1 | 0 |
| Leu | 3 | 3 | 2 | 3 | 0 |
| Tyr | 1 | 1 | 1 | 1 | 1 |
| Phe | 1 | 1 | 1 | 1 | 1 |
|  | 71–72 | 71–72 | 72–73 | 74–75 | 49 |

EXAMPLE 7

Comparison of Purified PAI to Echistatin

Figure 18:
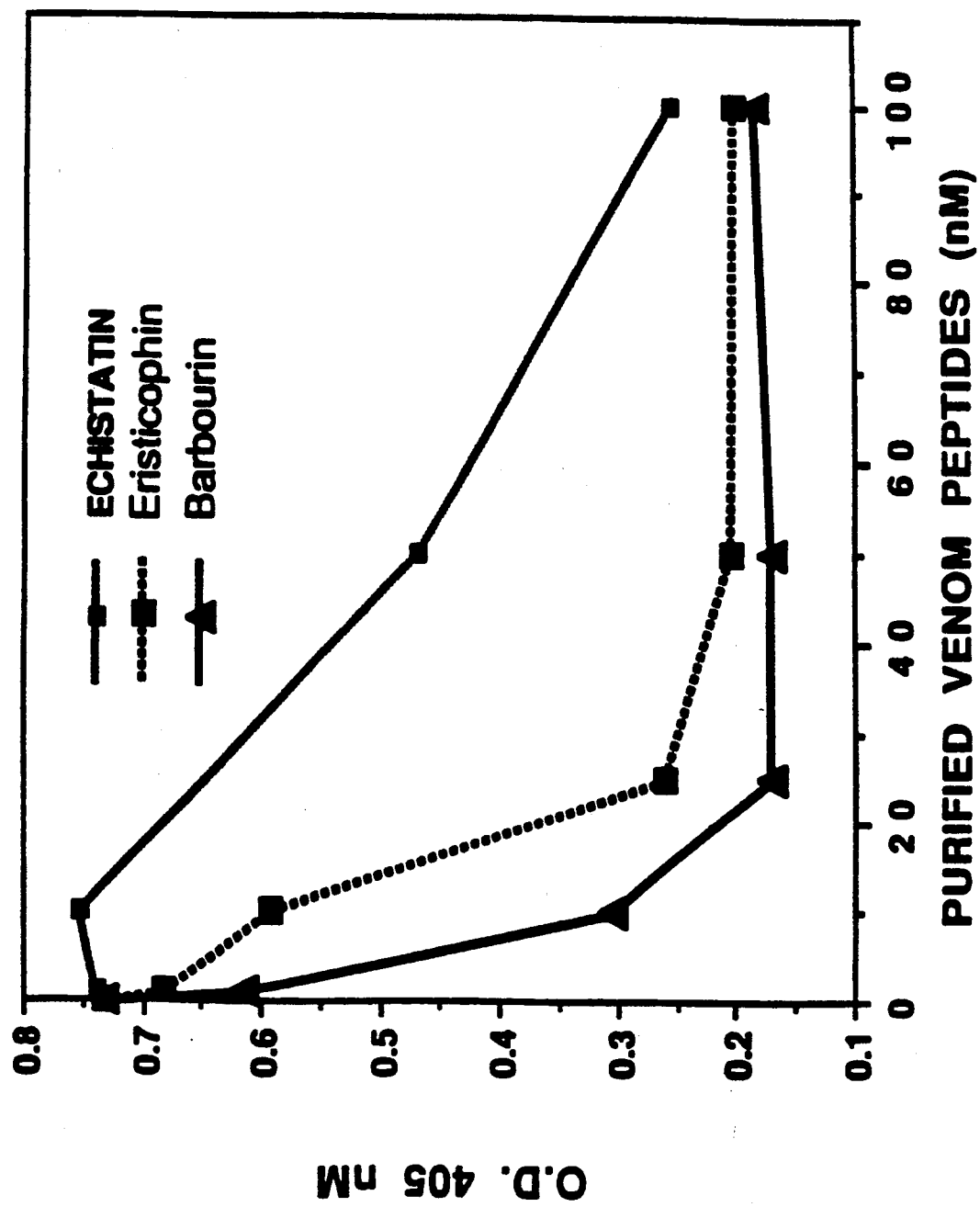
FIG. 18 shows the dose-response effects of purified snake venom peptides to inhibit fibrinogen/GP IIb–IIIa binding as compared to echistatin.

The peptides purified as described in Examples 2 and 4 were compared to the 49-residue peptide echistatin in inhibiting fibrinogen binding to GP IIb-IIIa, as described in Example 1, paragraph A. FIG. 18 shows that these purified PAIs are 2–3 times more potent in this assay than the standard echistatin.

Peptides purified to homogeneity from *Echis carinatus*, *Sistrurus m. barbouri*, and *Eristicophis macmahoni* venoms were compared to echistatin in the ADP-stimulated platelet aggregation assay. Increasing concentrations of purified snake venom peptides were added (without preincubation) at the indicated concenamount of bound labeled vitronectin;
   (f) determining the inhibition in (e); and
   (g) selecting a sample in which the relative inhibition determined in (c) is at east twice that determined in (f).

2. A method for selecting a compound that selectively inhibits platelet aggregation over other cellular activities mediated by integrins, which method comprises:
   (a) contacting a sample of said compound with purified GP IIb-IIIa receptor coated onto a solid support in the presence of a solution of labeled fibrinogen or von Willebrand Factor under conditions wherein fibrinogen or von Willebrand factor binds to said GP IIb-IIIa;

(b) measuring the binding of fibrinogen or von Willebrand factor to GP IIb-IIIa in comparison to the binding of fibrinogen or von Willebrand factor to GP IIb-IIIa in a control which does not contain said compound by measuring the amount of bound labeled fibrinogen;

(c) determining the inhibition in (b);

(d) contacting a sample of said compound with purified fibronectin receptor coated onto a solid support in the presence of a solution of labeled fibronectin under conditions wherein fibronectin binds to said fibronectin receptor;

(e) measuring the binding of fibronectin to fibronectin receptor in comparison to the binding of fibronectin to fibronectin receptor in a control which does not contain said compound by measuring the amount of bound labeled fibronectin;

(f) determining the inhibition in (e); and (g) selecting a sample in which the relative inhibition determined in (c) is at least twice that determined in (f).

3. The method of claim 1, comprising the further steps of:

(h) contacting a sample selected in (g) with purified fibronectin receptor coated onto a solid support in the presence of a solution of labeled fibronectin under conditions wherein fibronectin binds to said fibronectin receptor;

(i) measuring the binding of fibronectin to fibronectin receptor in comparison to the binding of fibronectin to fibronectin receptor in a control which does not contain said compound by measuring the amount of bound labeled fibronectin;

(j) determining the inhibition in (i); and (k) selecting a sample in which the relative inhibition determined in (c) is at least twice that determined in (j).

* * * * *